US011246736B2

(12) United States Patent
Patmore et al.

(10) Patent No.: US 11,246,736 B2
(45) Date of Patent: Feb. 15, 2022

(54) PATIENT RESTRAINT SYSTEM AND METHODS FOR ASSISTING A CAREGIVER WITH PATIENT RESTRAINT

(71) Applicant: Stryker Corporation, Kalamazoo, MI (US)

(72) Inventors: Kevin Mark Patmore, Plainwell, MI (US); Sarah Elizabeth Mynhier, Kalamazoo, MI (US); Bryce Kelly Porter, Grand Rapids, MI (US); Kyle Stephen Spieker, Kalamazoo, MI (US); Douglas J. Paige, Lakewood, OH (US); Bernadette Rose Marconi, Salida, CO (US); Austin W. Frank, Shelby Township, MI (US); Miso Kim, Shelby Township, MI (US); Taylor Berry, Austin, TX (US); Matthew Charles Boden, Seven Hills, OH (US)

(73) Assignee: Stryker Corporation, Kalamazoo, MI (US)

( * ) Notice: Subject to any disclaimer, the term of this patent is extended or adjusted under 35 U.S.C. 154(b) by 1125 days.

(21) Appl. No.: 15/370,444

(22) Filed: Dec. 6, 2016

(65) Prior Publication Data

US 2017/0165097 A1   Jun. 15, 2017

Related U.S. Application Data

(60) Provisional application No. 62/265,225, filed on Dec. 9, 2015.

(51) Int. Cl.
*A61F 5/37* (2006.01)
*A61G 7/05* (2006.01)

(52) U.S. Cl.
CPC .......... *A61F 5/3769* (2013.01); *A61G 7/0526* (2013.01)

(58) Field of Classification Search
CPC .... A61F 5/3769; A61F 5/3761; A61F 5/3776; A61F 5/0118; A61F 5/013;
(Continued)

(56) References Cited

U.S. PATENT DOCUMENTS 4,204,534 A * 5/1980 Leary .................... A61F 5/3761
                                                          128/878
4,422,455 A * 12/1983 Olsen .................... A61F 5/3761
                                                          128/878
(Continued)

FOREIGN PATENT DOCUMENTS

CN      201267194 Y     7/2009
CN      202036387 U     11/2011
(Continued)

OTHER PUBLICATIONS

Qwikcuff, Medical Restraints re-invented, available as early as Dec. 9, 2015; URL: http://www.qwikcuff.com/wp-content/uploads/2015/04/Qwikcuff-Brochure-17x11-Final-V3-Web.pdf.
(Continued)

*Primary Examiner* — Caitlin A Carreiro
(74) *Attorney, Agent, or Firm* — Howard & Howard Attorneys PLLC

(57) ABSTRACT

A restraint apparatus operable by a user for restraining a limb of a person to a restraining point including a cuff having a first end and a second end. The cuff is operable between an open configuration and a closed configuration. The cuff is secured around the limb of the person in the closed configuration and the first end and the second end are separated from each other in the open configuration. At least one tether is attached to the cuff. The tether includes a coupler to couple the cuff to the restraining point when the
(Continued)

cuff is in the closed configuration. The cuff is wearable by a least a portion of a hand of the user in the open configuration.

19 Claims, 17 Drawing Sheets

(58) Field of Classification Search
CPC .. A61F 5/05866; A61F 5/107; A61F 5/05858; A61F 5/3723; A61F 5/37; A61B 5/6831; A61N 2005/1097; E05B 75/00; A61G 7/0526; A63B 21/04; A63B 21/4001; A63B 21/4025
USPC ............ 128/846, 869, 870, 876–879, 882; D29/120.2; 119/794, 796; 2/159, 162, 2/910; 602/36, 21, 62, 64, 75; 482/123, 482/124
See application file for complete search history.

(56) References Cited

U.S. PATENT DOCUMENTS

| | | | | |
|---|---|---|---|---|
| 4,884,581 | A | * | 12/1989 | Rescigno .............. A46B 5/04 128/869 |
| 4,887,616 | A | * | 12/1989 | Baijnath ............ A61F 5/05866 128/879 |
| 5,094,396 | A | | 3/1992 | Burke |
| 6,076,527 | A | | 6/2000 | Rottinghaus et al. |
| 6,740,056 | B2 | * | 5/2004 | Slautterback ......... A61F 5/0118 128/879 |
| 8,727,981 | B2 | | 5/2014 | Bechtel et al. |
| 8,833,310 | B2 | * | 9/2014 | Konigsberg ......... A01K 27/003 119/770 |
| 2012/0215253 | A1 | * | 8/2012 | McEwen ............ A61B 17/1355 606/202 |
| 2012/0318798 | A1 | | 12/2012 | Domoy |
| 2013/0110019 | A1 | * | 5/2013 | Hopman ............ A61B 17/1327 602/13 |
| 2014/0011021 | A1 | | 1/2014 | Determan et al. |

FOREIGN PATENT DOCUMENTS

| | | |
|---|---|---|
| CN | 202740187 U | 2/2013 |
| CN | 203763337 U | 8/2014 |
| CN | 203790115 U | 8/2014 |
| WO | 2007075701 A2 | 7/2007 |

OTHER PUBLICATIONS

RehabMart.com, LLC, Posey Quick-Release T-A-T Cuff, 1998-2017, URL: http://www.rehabmart.com/product/posey-quickrelease-tat-cuff-11475.html.
Vitality Medical, Posey Quick-Release Limb Holders, 2015, URL: http://www.vitalitymedical.com/posey-twice-as-tough-cuffs-for-stretcher.html.
Vitality Medical, Posey Twice-as-Tough Cuffs for Stretcher, 2015, URL: http://www.vitalitymedical.com/posey-twice-as-tough-cuffs-for-stretcher.html.
Posey Products, LLC, Posey Non-Locking Twice-as-Tough Cuffs-Wrist, 2017, URL: http://www.posey.com/products/patient-safety-and-protection/edpsych/2790-2790-posey-non-locking-twice-tough%C2%AE-cuffs-wrist.
Avery Dennison, Monarch SG Attacher, 2008, 2 pages, URL: http://www.monarch.averydennison.com/products/documents/IPSDocuments/attacher_2008.pdf.
English language abstract and machine-assisted translation for CN201267194 extracted from espacenet.com database Mar. 7, 2017, 8 pages.
English language abstract and machine-assisted translation for CN203790115 extracted from espacenet.com database Mar. 7, 2017, 9 pages.
English language abstract and machine-assisted translation for CN203763337 extracted from espacenet.com database Mar. 7, 2017, 12 pages.
English language abstract and machine-assisted translation for CN202740187 extracted from espacenet.com database Mar. 7, 2017, 8 pages.
English language abstract and machine-assisted translation for CN202036387 extracted from espacenet.com database Mar. 7, 2017, 15 pages.
Black Diamond Equipment, Stoppers, URL: https://www.blackdiamondequipment.com/en_US/climbing-cams-stoppers-nuts-hexes/stoppers-BD225202_cfg.html.
Black Diamond Equipment, Hoodwire Carabiner; Available as early as Dec. 9, 2015; URL: http://www.blackdiamondequipment.com/en/climbing-carabiners-quickdraws/hoodwire-BD210147POLSALL1.html.
Fidlock Fasteners, SNAP push, available as early as Dec. 9, 2015; URL: http://www.fidlock.com/en/fasteners/snap-push.html.
Cobra 50mm Mil-Spec Buckle, Odin Tactical, available as early as Dec. 9, 2015; URL: http://www.odintactical.co.uk/cobra-50mm-milspec-buckle.
National Webbing Products Co. (TM), SR Black Plastic Side Release Buckle; available as early as Dec. 9, 2015 URL: http://www.nationalwebbing.com/products/SR-Black-Plastic-Side-Release-Buckle.html.
Memapets, ALU(R) Collar with NFC Technology; available as early as Dec. 9, 2015; URL: http://www.memapets.com/.
Car Builder Solutions, Rubber Bonnet/Boot Hooks Pair; available as early as Dec. 9, 2015; URL: https://www.carbuildersolutions.com/de/rubber-bonnet-boot-hooks-pair.
Posey Products, LLC, 2216 Posey Clean Cuffs Set, available as early as Dec. 9, 2015; URL: https://www.posey.com/products/patient-safety-and-protection/edpsych/2216-2216-posey-clean-cuffs-set.
Pinel Medical, Restraining & De-Restraining Instruction Manual; available as early as Dec. 9, 2015; 36 pages.

* cited by examiner

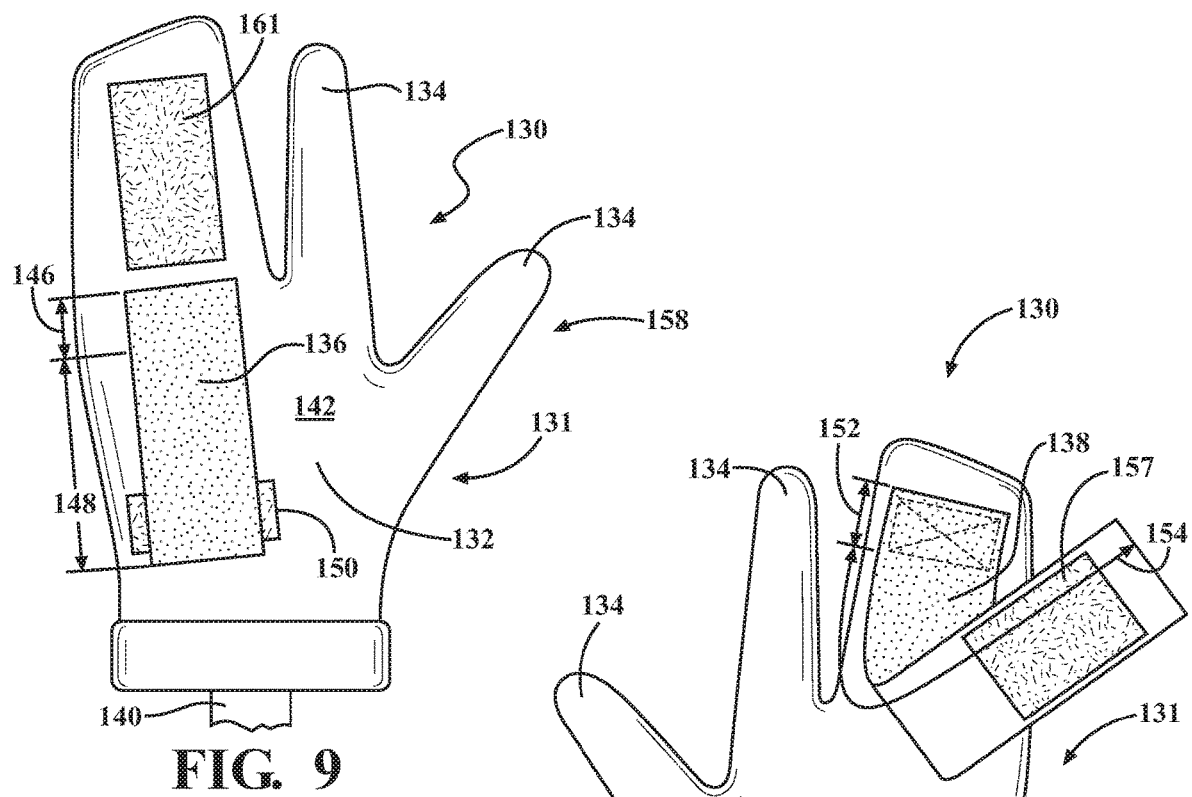
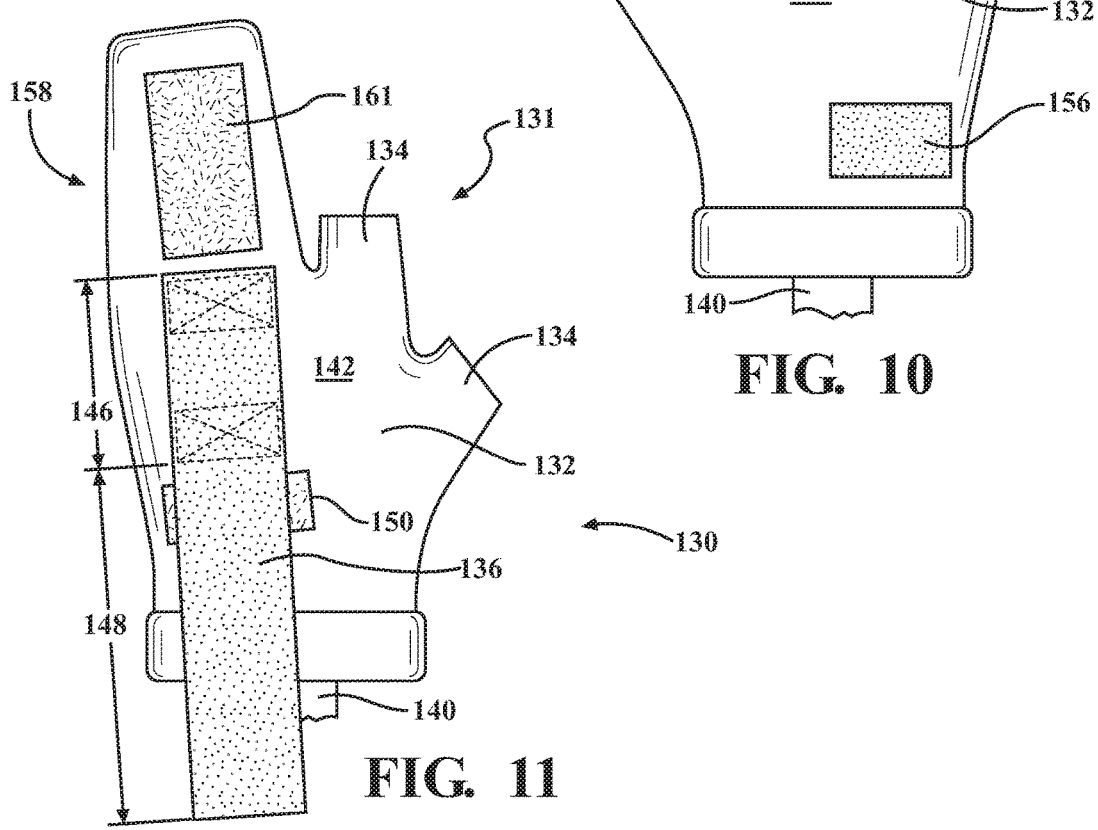
FIG. 9
FIG. 10
FIG. 11

PATIENT RESTRAINT SYSTEM AND METHODS FOR ASSISTING A CAREGIVER WITH PATIENT RESTRAINT

RELATED APPLICATIONS

This application claims the benefit of and priority to U.S. Provisional Patent Application No. 62/265,225, filed on Dec. 9, 2015, the entire contents and disclosure of which are hereby incorporated by reference.

BACKGROUND

Patient restraint systems are sometimes needed when a caregiver is faced with a combative patient and must physically restrain the patient. Currently, patient restraint systems require one person to hold a limb of the patient and an additional person to attach a cuff on the combative patient. The cuff then needs to be connected by a strap to a restraining point, often located on a patient support apparatus, such as a hospital bed, stretcher, cot, wheelchair, and the like. Often, the restraining points are inconspicuous or otherwise difficult to access.

In combative situations, the number of people available to assist in restraining the combative patient is usually insufficient to safely restrain the combative patient without injury to the caregiver and/or the combative patient. Without sufficient personnel, placement of the cuff on the combative patient and connection of the cuff to the restraining point, is even more difficult. Moreover, without sufficient personnel, additional time is likely required to restrain the combative patient, increasing the likelihood of injury to the caregiver and/or the combative patient.

A patient restraint system designed to allow for restraint of combative patients that is simple, safe, and secure while overcoming one or more of the aforementioned challenges is desired.

BRIEF DESCRIPTION OF THE DRAWINGS

FIG. 9 is a top view of an alternative restraint apparatus.

FIG. 10 is a bottom view on the alternative restraint apparatus.

FIG. 11 is a top view of another embodiment of the alternative restraint apparatus.

DETAILED DESCRIPTION

Figure 1:
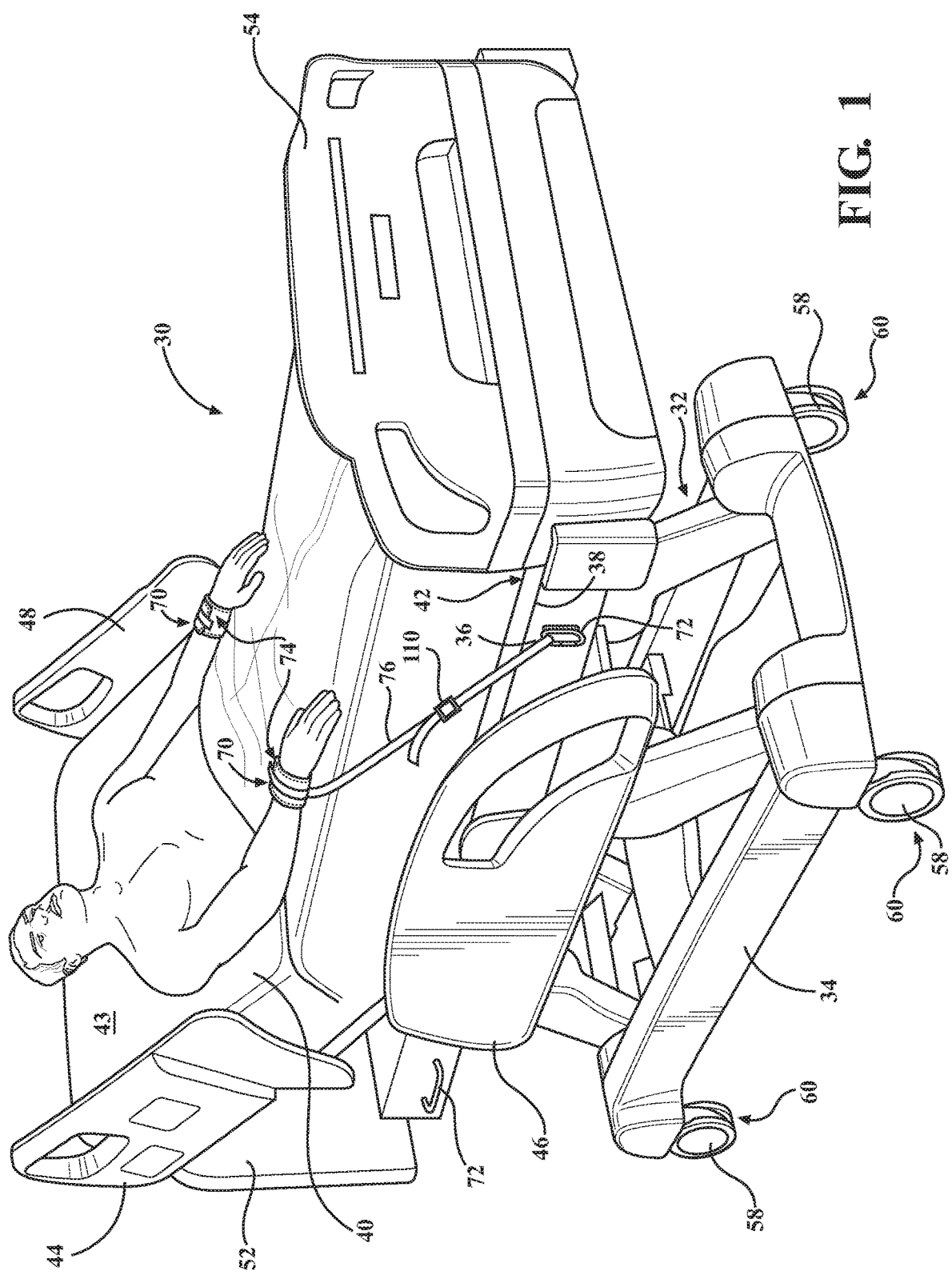
FIG. 1 is a perspective view of a patient support apparatus.

Referring to FIG. 1, a patient support system comprising a patient support apparatus 30 is shown for supporting a patient in a health care setting. The heath care setting may be a hospital, a clinic, an emergency vehicle, a site requiring emergency medical services, or the like. The patient support apparatus 30 illustrated in FIG. 1 comprises a hospital bed. In other embodiments, however, the patient support apparatus 30 may comprise a stretcher, cot, table, wheelchair, or similar apparatus utilized in the care of a patient.

A support structure 32 provides support for the patient. The support structure 32 illustrated in FIG. 1 comprises a base 34 and an intermediate frame 36. The intermediate frame 36 is spaced above the base 34. The support structure 32 also comprises a patient support deck 38 disposed on the intermediate frame 36. The patient support deck 38 comprises several sections, some of which are pivotable relative to the intermediate frame 36, such as a fowler section, a seat section, a thigh section, and a foot section. The patient support deck 38 provides a patient support surface 42 upon which the patient is supported.

A mattress 40 is disposed on the patient support deck 38. The mattress 40 comprises a secondary patient support surface 43 upon which the patient is supported. The base 34, intermediate frame 36, patient support deck 38, and patient support surfaces 42, 43 each have a head end and a foot end corresponding to designated placement of the patient's head and feet on the patient support apparatus 30. The construction of the support structure 32 may take on any known or conventional design, and is not limited to that specifically set forth above. In addition, the mattress 40 may be omitted in certain embodiments, such that the patient rests directly on the patient support surface 42.

Side rails 44, 46, 48, are coupled to the intermediate frame 36 and thereby supported by the base 34. A first side rail 44 is positioned at a right head end of the intermediate frame 36. A second side rail 46 is positioned at a right foot end of the intermediate frame 36. A third side rail 48 is positioned at a left head end of the intermediate frame 36. A fourth side rail (not shown) is positioned at a left foot end of the intermediate frame 36. If the patient support apparatus 30 is a stretcher or a cot, there may be fewer side rails. The side rails 44, 46, 48, are movable between a raised position in which they block ingress and egress into and out of the patient support apparatus 30, and a lowered position in which they are not an obstacle to such ingress and egress. The side rails 44, 46, 48 may also be movable to one or more intermediate positions between the raised position and the lowered position. In still other configurations, the patient support apparatus 30 may not include any side rails.

A headboard 52 and a footboard 54 are coupled to the intermediate frame 36. In other embodiments, when the headboard and footboard 54 are included, the headboard 52 and footboard 54 may be coupled to other locations on the patient support apparatus 30, such as the base 34. In still other embodiments, the patient support apparatus 30 does not include the headboard 52 and/or the footboard 54.

Wheels 58 are coupled to the base 34 to facilitate transport over the floor surfaces. Four wheels 58 are arranged in each of four quadrants of the base 34 adjacent to corners of the base 34. In the embodiment shown, the wheels 58 are caster wheels able to rotate and swivel relative to the support structure 32 during transport. Each of the wheels 58 forms part of a caster assembly 60. Each caster assembly 60 is mounted to the base 34. It should be understood that various configurations of the caster assemblies 60 are contemplated. In addition, in some embodiments, the wheels 58 are not caster wheels and may be non-steerable, steerable, non-powered, powered, or combinations thereof. Additional wheels are also contemplated. For example, the patient support apparatus 30 may comprise four non-powered, non-steerable wheels, along with one or more powered wheels.

In other embodiments, one or more auxiliary wheels (powered or non-powered), which are movable between stowed positions and deployed positions, may be coupled to the support structure 32. In some cases, when these auxiliary wheels are located between caster assemblies 60 and contact the floor surface in the deployed position, they cause two of the caster assemblies 60 to be lifted off the floor surface thereby shortening a wheel base of the patient support apparatus 30. A fifth wheel may also be arranged substantially in a center of the base 34.

As additionally illustrated in FIG. 1, a restraint apparatus 70 may be provided with the patient support system. The restraint apparatus 70 is operable by a user to restrain a person, such as the patient, to a restraining point 72. The restraining point 72 may be a part of a bed, a wall, a stretcher, or any other surface upon which the restraint apparatus 70 could be secured. In particular, the restraint apparatus 70 is useful when the person is combative and the user, such as a caregiver, must physically restrain the person.

The restraint apparatus 70 comprises a cuff 74 and a tether comprising a strap 76. The cuff 74 is configured to be placed on a limb or body of the person being restrained by the user, such as around a forearm, wrist, or leg (e.g., ankle) of the person. Once the cuff 74 is successfully placed on the person, the user can grab and manipulate the strap 76 to attach the strap 76 to the restraining point 72 thereby coupling the cuff 74 to the restraining point 72. With the cuff 74 safely on the limb and coupled to the restraining point 72, the person is restrained from causing harm to the user or others.

Figure 2:
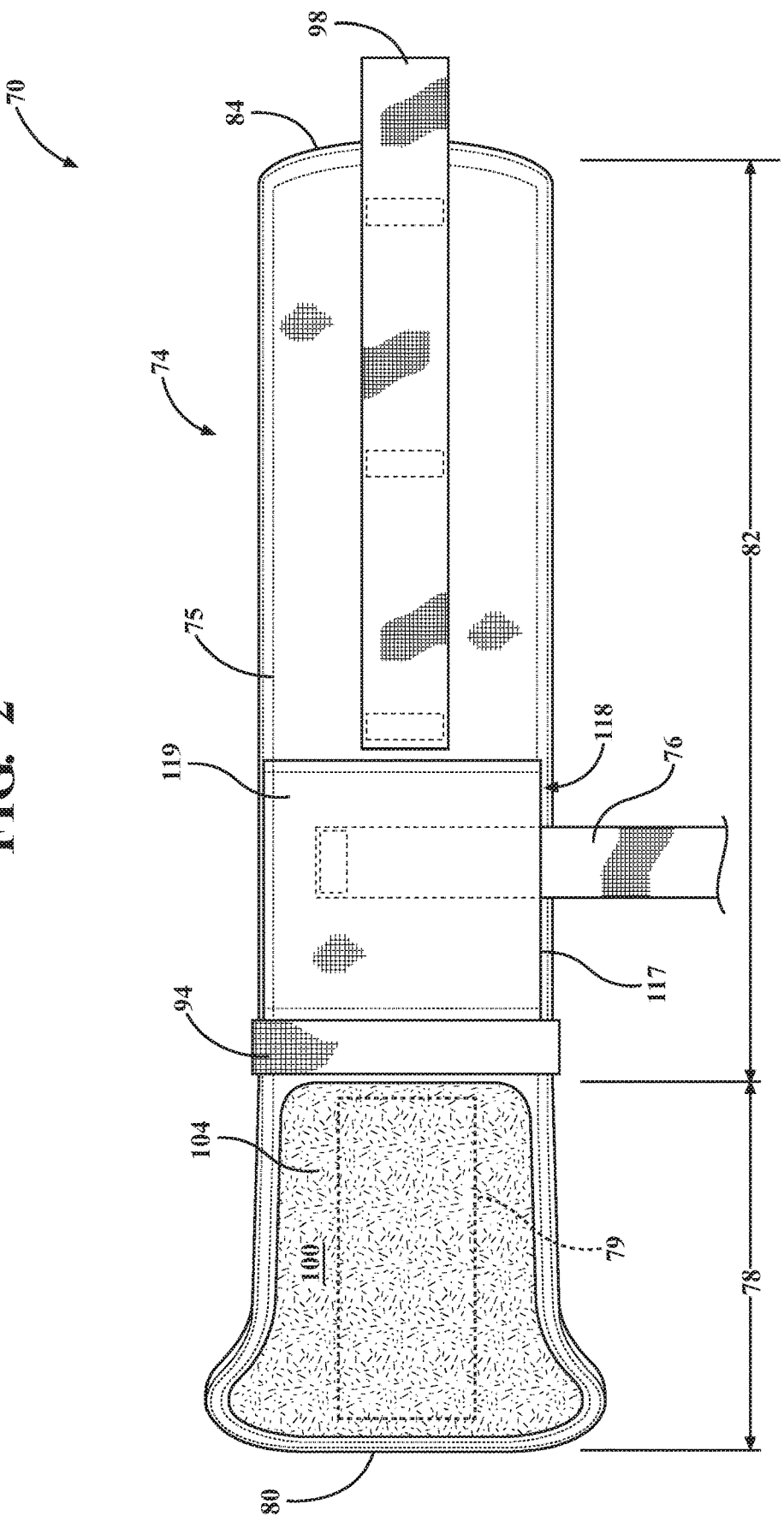
FIG. 2 is a top view of a restraint apparatus.
Figure 3:
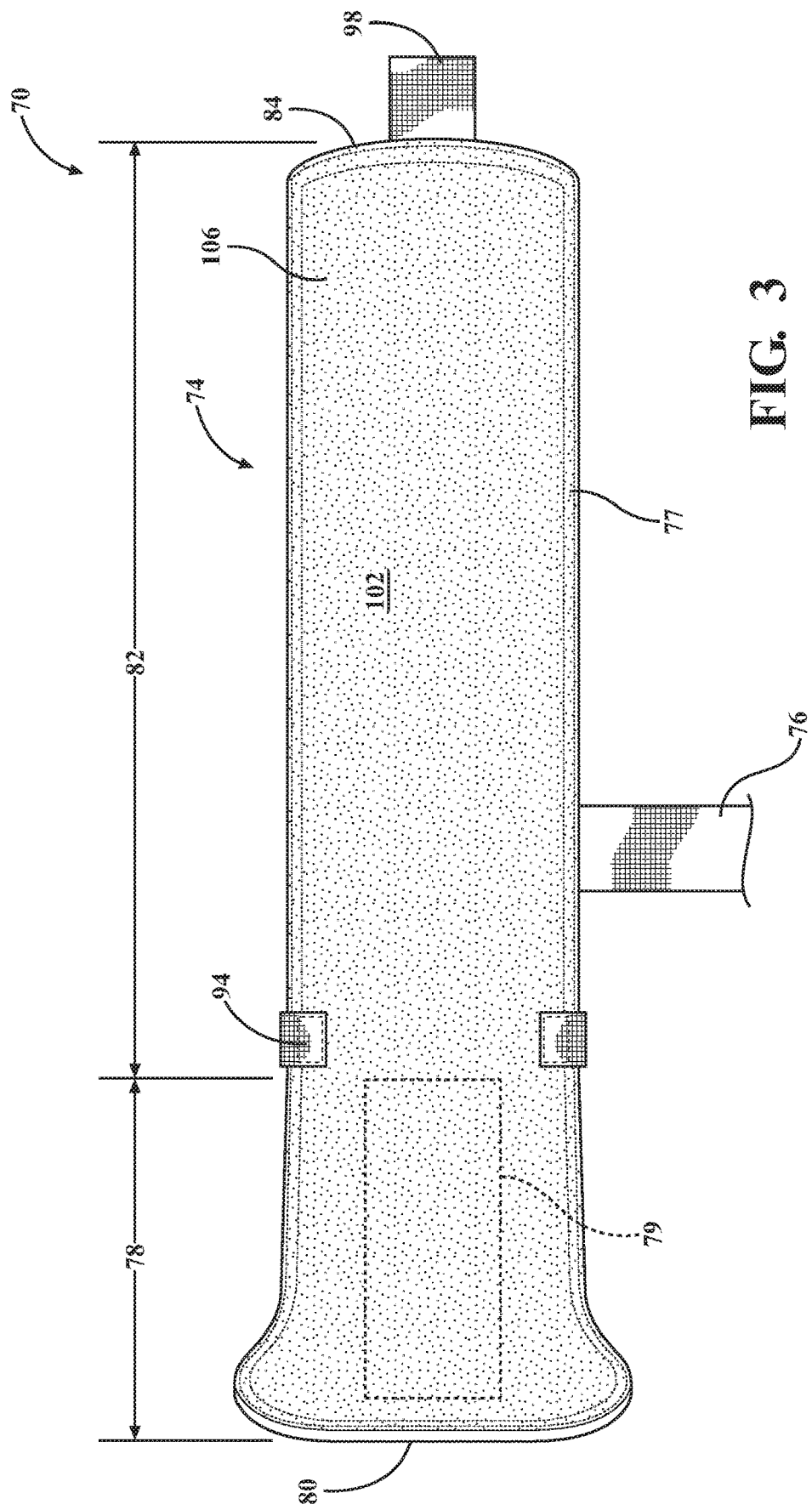
FIG. 3 is a bottom view of the restraint apparatus.
Figure 4:
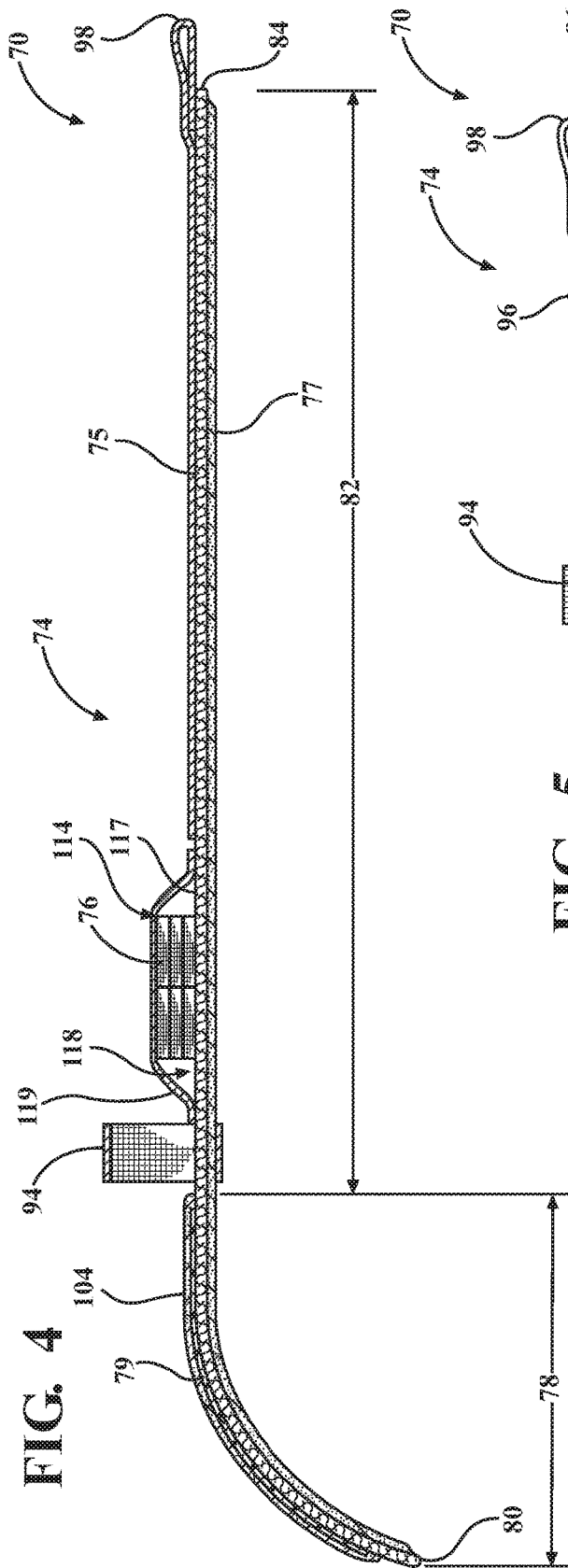
FIG. 4 is a cross-sectional view of the restraint apparatus.

Referring to FIGS. 2-4, the cuff 74 comprises a first layer 75 of material and a second layer 77 of material. The layers 75, 77 may be comprised of soft or semi-soft fabric providing a comfortable fit for the person. It is contemplated that the layers 75, 77 may be made of cotton, cloth, felt, fleece, nylon, wool, foam, or any other material which provides a comfortable fit to the person, including blends of any of the above described materials. In other embodiments, the cuff 74 may be comprised of a single layer of material or may include filling or padding between the layers 75, 77. The first layer 75 may be attached to the second layer 77 via sewing, ultrasonic welding, heat sealing, adhesive, or other suitable methods. In the embodiment shown, the layers 75, 77 are congruent and are sewn together about their outer peripheries.

The cuff 74 comprises a first section 78 having a first end 80 and a second section 82 having a second end 84. The first section 78 is generally less than half of a length of the cuff 74 from the first end 80 to the second end 84. In the embodiment illustrated, the first section 78 is approximately one third of the length of the cuff 74. However, it is also contemplated that the first section 78 may be longer or shorter. In the embodiment shown, both of the layers 75, 77 extend from the first end 80 to the second end 84 and span both of the sections 78, 82.

As shown in FIG. 4, the first section 78 may comprise a preformed curved section that is shaped to conform to the limb of the person being restrained (e.g., by being concave or C-shaped), thereby easing fitting of the cuff 74 to the limb of the person as described further below. In one embodiment, the preformed curved section is formed by a preformed insert 79. The insert 79 may be at least partially formed of plastic, such as PVC, PEEK, HDPE, or other suitable plastic material. In other embodiments, the insert 79 is fully formed of plastic materials, or may be formed of non-plastic materials, such as metal.

The insert 79 may be attached to the first layer 75, the second layer 77, or both of the layers 75, 77 by sewing, ultrasonic welding, heat sealing, adhesive, or the like. In other embodiments, the preformed curved section is formed by one or more of the layers 75, 77 being formed in the curved shape at the first section 78. It is also contemplated that the first section 78 may be flat, convex, or of any other shape in other embodiments. In the embodiment shown, the insert 79 assumes a curved configuration in its normal state, as shown in FIG. 4. The insert 79 has a generally rectangular shape when flattened from its curved configuration, but may have other shapes in other embodiments. The insert 79 is disposed on the first layer 75 and sewn to the first layer 75. In other embodiments, the insert 79 may float freely between the first layer 75 and the second layer 77 or may be attached to one or both of the layers 75, 77 in other ways.

Figure 4A:
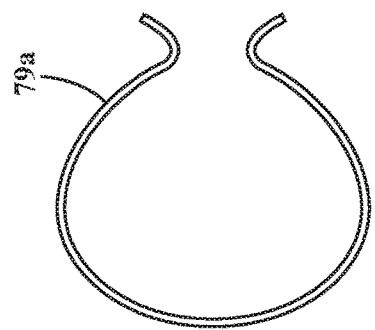
FIG. 4A is a side view of an alternative insert for the restraint apparatus.

In other embodiments, alternative inserts could be used to define the preformed curved section. In some cases, the preformed curved section extends at least partially into the second section 82, or completely into the second section 82. For instance, an insert 79a like that shown in FIG. 4A, may extend from the first end 80 to the second end 84 between the layers 75, 77 and be shaped much like a bracelet so that the first and second ends 80, 84 nearly contact one another (or do contact one another in some cases) in a severe C-shape. In this case, the insert 79a would be capable of being separated and further opened in the open configuration to fit onto the limb of the person being restrained when attaching the restraint apparatus. For example, the opposing ends of the insert 79a could be flared outwardly as shown, which would similarly flare the first and second ends 80, 84 of the first and second sections 78, 82 so that the flared ends are able to engage the limb and open automatically under the force of engaging the limb when applying the restraint apparatus. Once around the limb, the insert 79a would return to its normal state and at least partially encircle the limb of the person being restrained.

In still further embodiments, instead of a preformed curved section, or in addition to the preformed curved section, the first section 78 may comprise articulating elements that are manipulated to conform to the limb of the person being restrained. The articulating elements could be stiffly connected at pivot points or loosely connected, much like links of a watch. The articulating elements could be designed to close around the limb of the person to be restrained and fasten, either automatically, such as by using magnets, or with a clasp, like on a watch. The first section 78 could also comprise a spring band between the layers 75, 77. The spring band is resilient and formed of metal. The spring band assumes a straight, cross-sectionally convex shape before applying to the limb of the person to be restrained, but when applied to the limb such that the convex shape is flattened out, the spring band snaps (or slaps) around the limb. This construction is the same as a snap bracelet (aka slap bracelet).

Returning to FIG. 4, the second section 82 constitutes the remainder of the length of the cuff 74 adjacent the first section 78. The second section 82 may be a flexible section formed primarily of the layers 75, 77 without any additional inserts or other materials between the layers 75, 77. Of course, in other embodiments, one or more inserts could be present.

The cuff 74 comprises a top surface 100 (see FIG. 2) and a bottom surface 102 (see FIG. 3). The top surface 100 of the cuff 74 comprises a first fastener 104. The first fastener 104 may comprise the entire top surface 100 or may only comprise a portion of the top surface 100. In the embodiment shown, the first fastener 104 only extends as far as the first section 78. In the embodiment shown, the insert 79 is captured between the first fastener 104 and the first layer 75.

The bottom surface 102 of the cuff 74 comprises a second fastener 106. The second fastener 106 may comprise the entire bottom surface 102 or may only comprise a portion of the bottom surface 102. In the embodiment shown, the bottom surface 102 is the bottom surface of the second layer 77 and the second fastener 106 extends the entire length of the bottom surface 102. The second fastener 106 spans across the first section 78 and the second section 82 in the embodiment shown.

The first fastener 104 is configured to be engaged by the second fastener 106 when the cuff 74 is placed around the limb of the person to be restrained. The fasteners 104, 106 may be any type of complimentary fasteners including but not limited to hook and loop fasteners (e.g., Velcro®), snaps, or adhesive.

Figure 5:
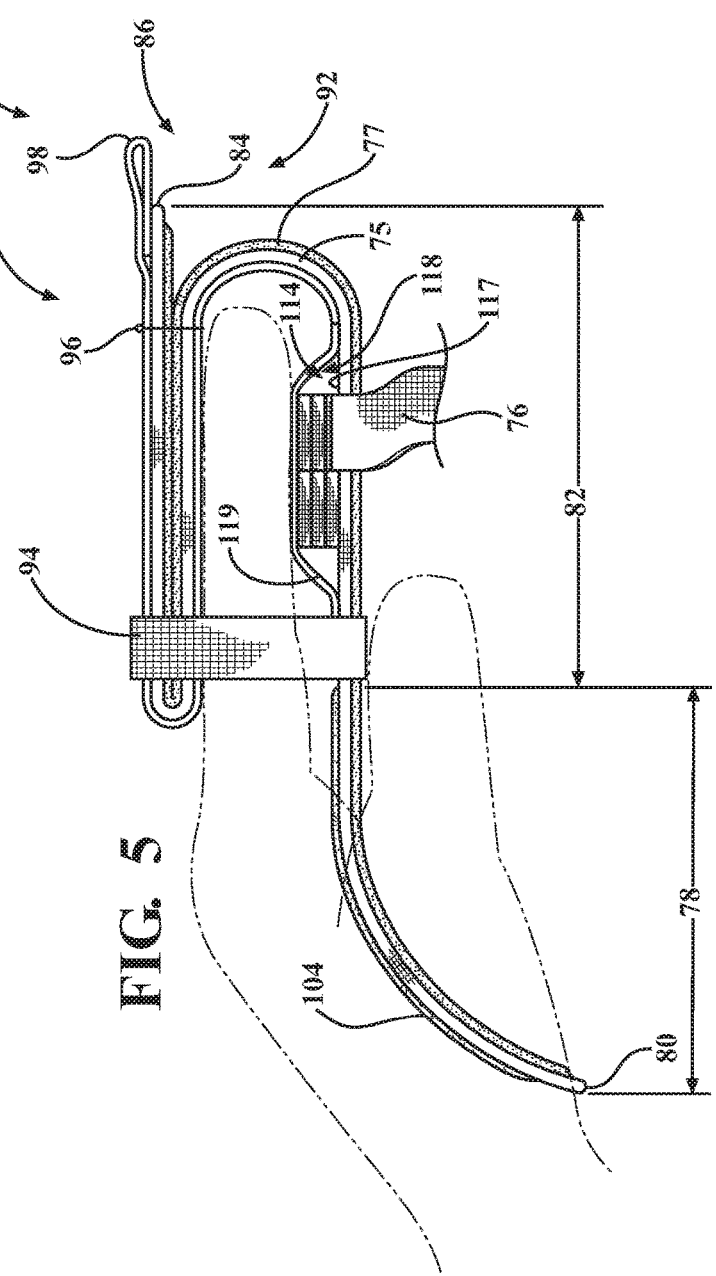
FIG. 5 is a side view of the restraint apparatus in an open configuration worn by a user.

To facilitate ease of use, the cuff 74 may be provided to users with the second section 82 folded upon itself in a folded configuration 92, as illustrated in FIG. 5. A folded portion of the second section 82 is placed beneath and temporarily secured by an engaging element 94. The engaging element 94 may include one or more elastic straps or other engaging elements for holding the second section 82 in the folded configuration 92. Moreover, the second section 82 may be secured in the folded configuration 92 using at least one temporary fastener 96. The temporary fastener 96 may include one or more of a plastic fastener, a snap, a hook and loop fastener (e.g., Velcro®), and a threaded fastener. The temporary fastener 96 may also include any other temporary fasteners.

Figure 6:
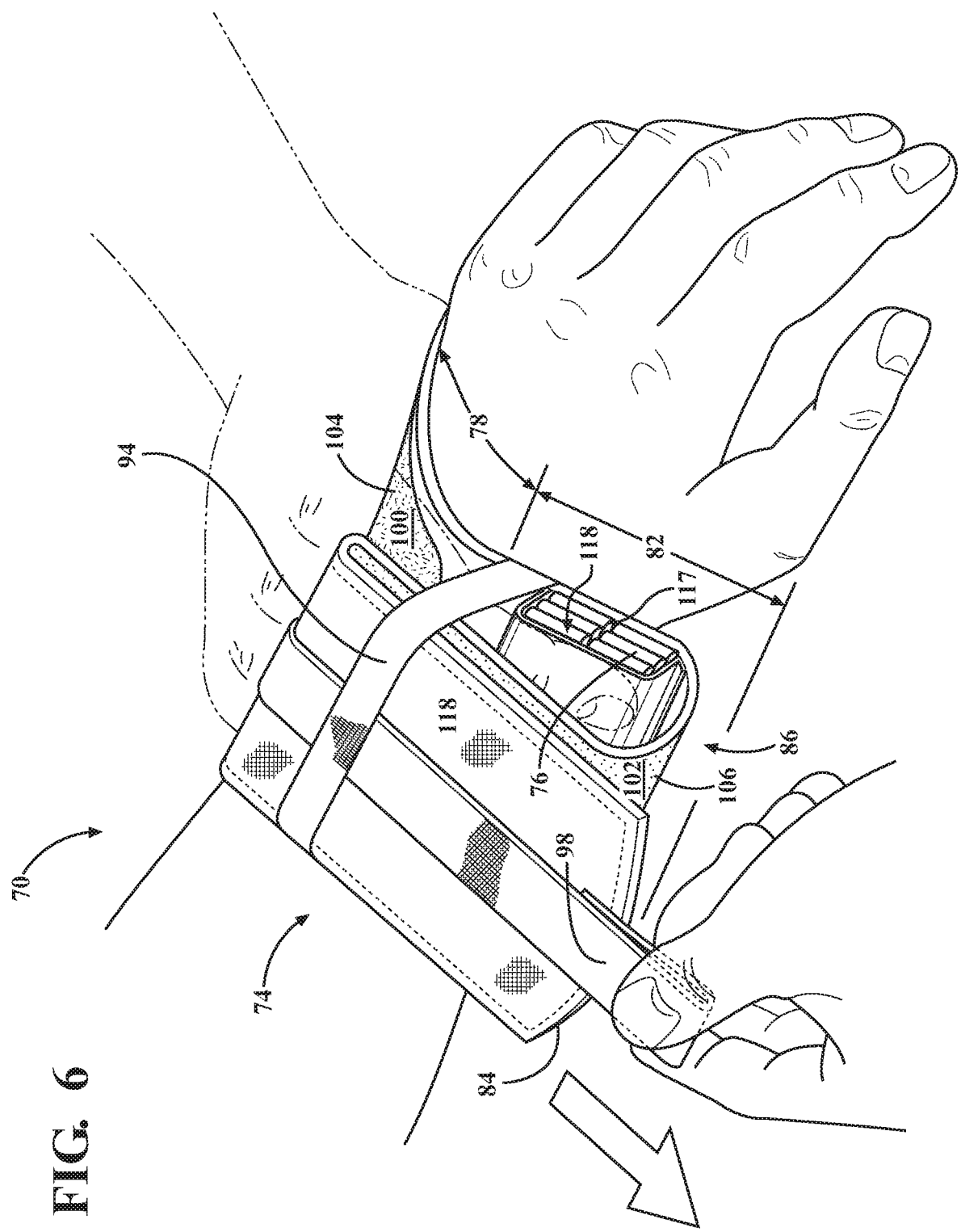
FIG. 6 is a perspective view of the restraint apparatus illustrating placement of a cuff of the restraint apparatus on a limb of a person.
Figure 7:
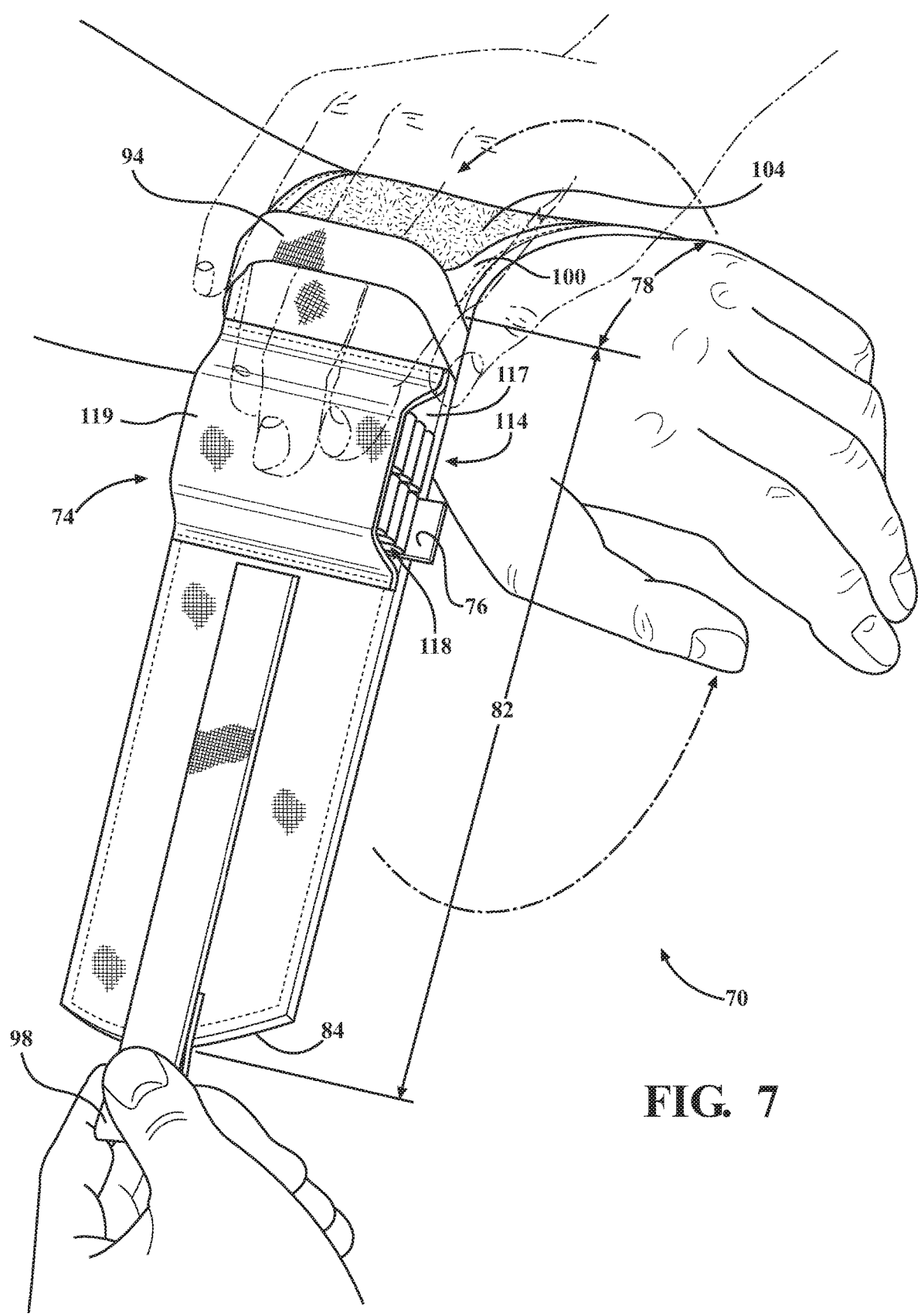
FIG. 7 is a perspective view of the restraint apparatus illustrating transition of the cuff from the open configuration toward a closed configuration about the limb of the person.

As illustrated in FIGS. 5-7, the cuff 74 is wearable by at least a portion of the hand of the user in an open configuration 86 so that the cuff 74 is disposed between the hand of the user and the limb of the person when the user applies the cuff 74 onto the limb of the person to be restrained. Referring specifically to FIG. 5, the first end 80 and the second end 84 are separated from each other in the open configuration 86. In the embodiment shown, the first section 78 and the second section 82 are also detached from one another in the open configuration 86 to enable the user to place the cuff 74 on the limb of the person in the open configuration 86.

The engaging element 94, in addition to holding the second section 82, is configured to hold the cuff 74 on the hand of the user in the open configuration 86. The engaging element 94 and the second section 82 (in the folded configuration 92) at least partially cover the portion of the hand of the user when the cuff 74 is worn by the user. In particular when the cuff 74 is in the open configuration 86, one, two, three, four, or five fingers of the hand are inserted beneath a folded portion of the second section 82 with the second section 82 being secured in the folded configuration 92 by the engaging element 94, the temporary fasteners 96, or both. In the Figures, the thumb and little finger of the user are free, but could be engaged by other engagement elements in other embodiments.

In one embodiment, owing to the precurved or conformed shape of the first section 78, the first section 78 is comfortably received in and conforms to a palm of the hand of the user when the cuff 74 is worn by the user in the open configuration 86.

Figure 6A:
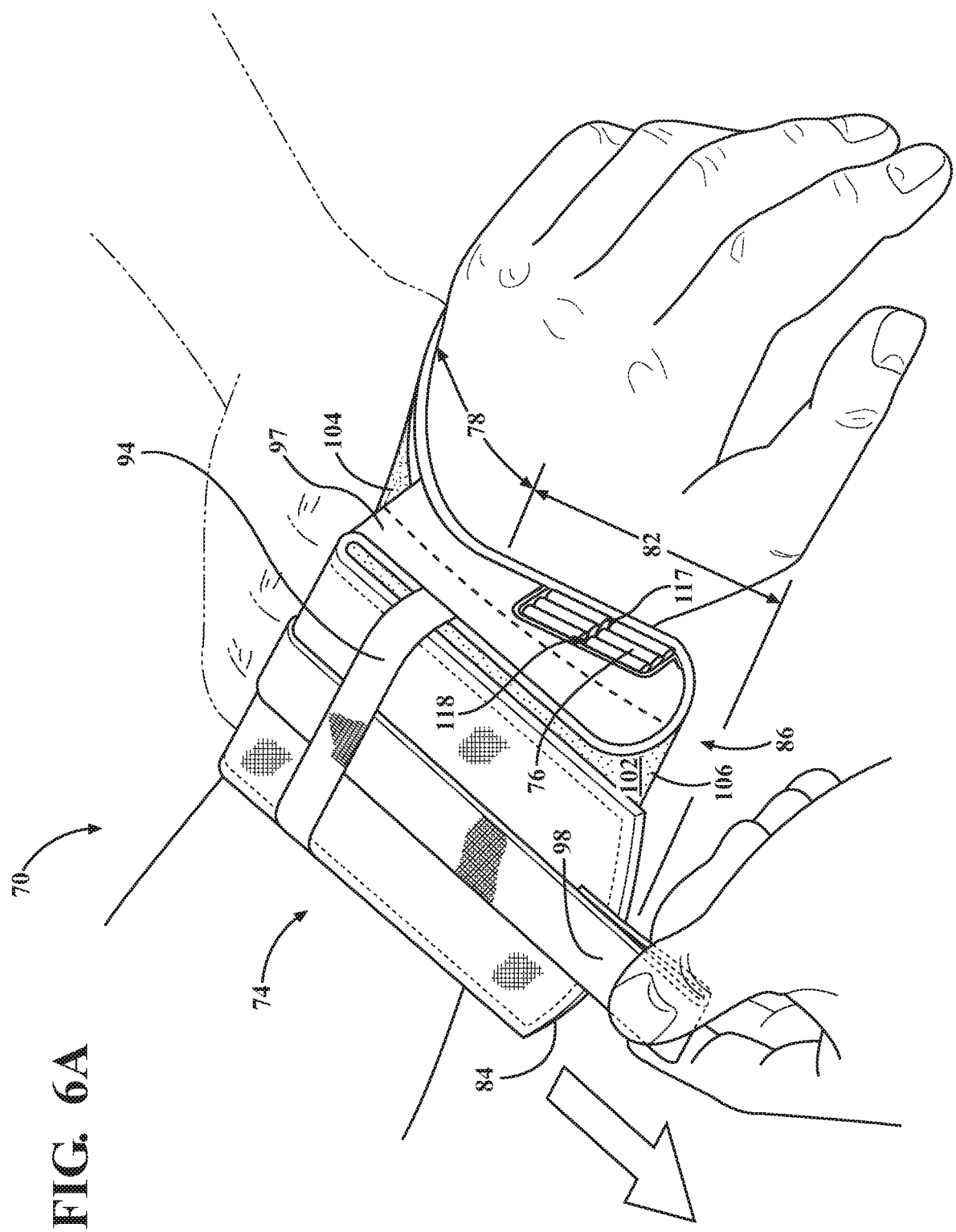
FIG. 6A is a perspective view of an alternative restraint apparatus illustrating a tear-away side wall.

It is also contemplated that the cuff 74 may be wearable by the user in other ways, including but not limited to, having at least a partial glove portion, one or more finger sections, at least a partial mitten portion, or adhesive. See, for example, the version in FIG. 6A in which a tear-away side wall 97 is added to the cuff 74 to temporarily provide a pocket for the user's fingers. The cuff 74 may additionally include a thumb engaging element (such as an additional strap) to help secure the cuff 74 to the hand of the user. Suitable adhesives to temporarily secure the cuff 74 to the user may comprise pressure sensitive adhesives, such as those from the 3M Company of Maplewood, Minn. See, for example, U.S. Patent Application Publication No. 2014/0011021 to Determan et al., filed Jul. 19, 2013, entitled "Gentle To Skin Adhesive," hereby incorporated by reference herein.

As described herein, the cuff 74 is wearable in any manner such that the hand of the user is still usable when the cuff 74 is worn. More specifically, when the cuff 74 is worn on the hand of the user, the user is still able to use that same hand to engage and grab the limb of the person without difficulty. The cuff 74 may be configured to be worn by either a left hand or right hand of the user. In some cases, the cuff 74 may be configured to work with only one hand or the other. In other embodiments, the cuff 74 may be wearable on a wrist or forearm of the user.

Figure 8:
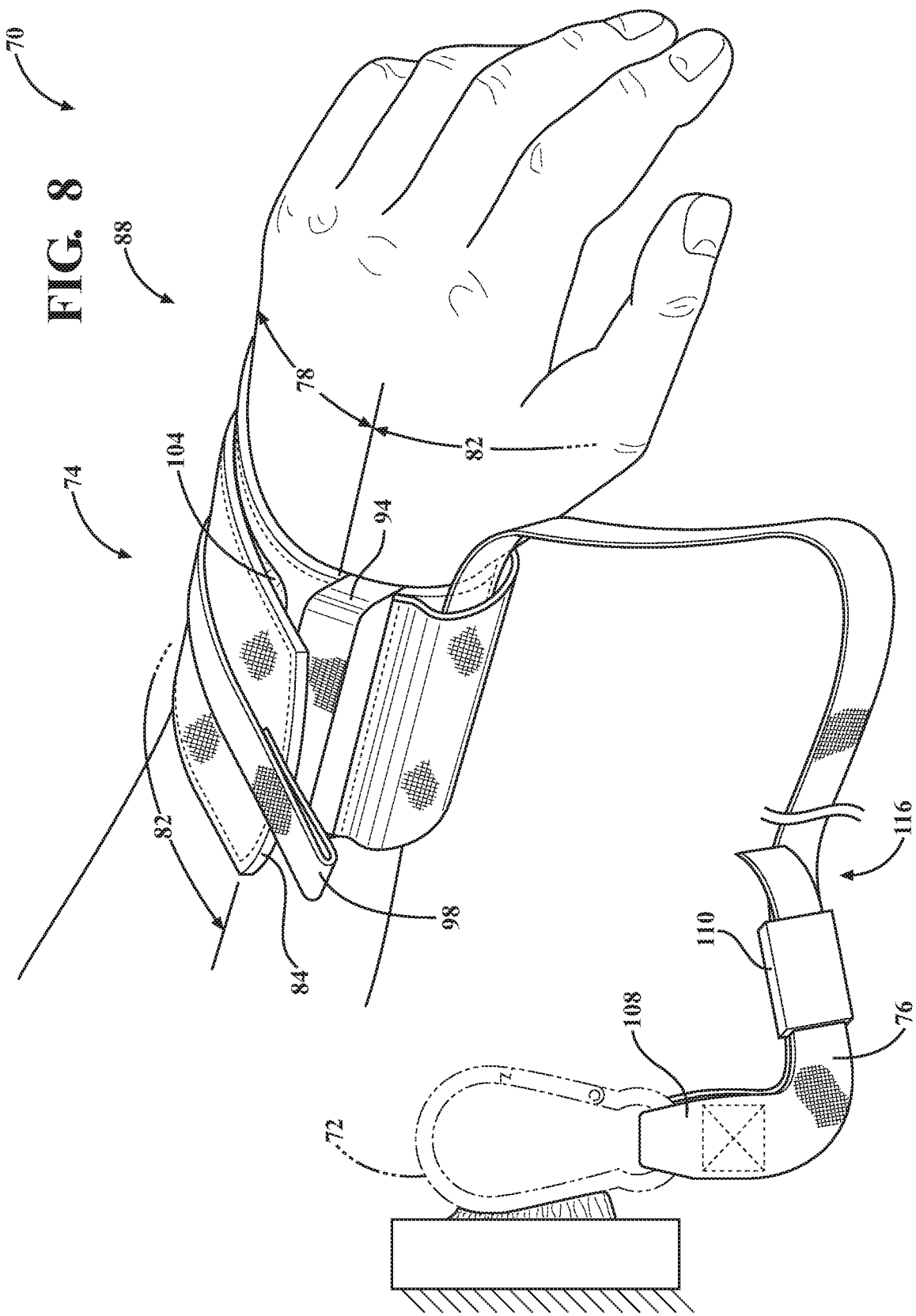
FIG. 8 is a perspective view of a restraint apparatus illustrating the cuff in the closed configuration about the limb of the person.

The cuff 74 is operable between the open configuration 86 and a closed configuration 88 (see FIGS. 6-8). The first section 78 and the second section 82 are secured to one another around the limb of the person in the closed configuration 88 to secure the cuff 74 to the limb (see FIG. 8). When the cuff 74 is in the closed configuration 88, the bottom surface 102 is moved by the user to engage the top surface 100 so that the cuff 74 completely surrounds the limb of the person. More specifically, when the cuff 74 is in the closed configuration 88, the second fastener 106 engages the first fastener 104 which secures the cuff 74 around the limb of the person. It is contemplated that the first fastener 104 and the second fastener 106 engage in any manner that allows the cuff 74 to be secured around the limb of the person.

A tab 98 is attached to the second section 82 to facilitate transitioning the cuff from the open configuration 86 to the closed configuration 88. The tab 98 extends beyond the second section 82 and the second end 84. The tab 98 is configured to be grabbed by an opposite hand of the user in order to transition the cuff 74 from the open configuration 86 to the closed configuration 88. The tab 98 may be attached to the first layer 75 and/or the second layer 77 by sewing, welding, adhesive or other suitable methods. The tab 98 may also be integrally formed with the first layer 75 and/or the second layer 77.

In the embodiment shown, the tab 98 is attached approximately along a center line of the second section 82 of the cuff 74 and extends at least half and almost the entire length of the second section 82. Having the tab 98 fixed along nearly the entire length of the second section 82 allows the tab 98 to withstand more pulling force without ripping or tearing. It is additionally contemplated that the tab 98 may be disposed on the second end 84.

Referring again to FIGS. 2-4, the strap 76 is attached to the cuff 74. In particular, the strap 76 has an attached end fixed to the cuff 74 such that the strap 76 is unable to be easily removed from the cuff 74. The strap 76 may be attached to one or both of the layers 75, 77 by sewing, welding, adhesive or other suitable methods. The strap 76 may also be integrally formed with one or both of the layers 75, 77. The strap 76 may be attached at the second section 82, the first section 78, or both sections 78, 82. Moreover the strap 76 may be attached to any surface of one or both of the layers 75, 77, or the strap 76 may be attached to the engaging element 94. In the embodiment shown, only a single strap 76 is included in the restraint apparatus 70. Additional straps may be employed in other embodiments.

The strap 76 extends from the attached end to an opposite, free end (it should be understood that the free end may refer to a folded or looped portion of the strap 76 at the opposite end). A coupler 108 (see FIG. 8) is located at the free end. The coupler 108 may be one or more of a loop, such as a loop of the strap 76, a D-ring, a magnetic lock device, a carabineer, a hook or any other coupling mechanism. Thus, the coupler 108 may be a component separate from the strap 76 or formed by the strap 76.

The strap 76 may be comprised of nylon, cloth, or any other material capable of restraining the person by keeping the cuff 74 coupled to the restraining point 72. A strap adjuster 110 is configured to adjust an effective length of the strap 76. The effective length of the strap 76 may be adjusted before or after the strap 76 is coupled to the restraining point 72. Moreover, it is contemplated that the strap 76 may be extendable from or retractable into a retracting mechanism (not shown) disposed on the cuff 74. In that case, the strap 76 may comprise at least one pull-tab configured to extend and retract the strap 76 from the retracting mechanism, similar to a retractable cord, tape measure, or the like, such that an effective length of the strap is changed. The coupler 108 may also be configured to change the effective length of the strap 76. For instance, the coupler 108 may comprise multiple coupling parts, each coupling part located to yield different effective lengths when attached to the restraining point 72. One example of such a coupler is a chain of links. Accordingly, the user selects one of the coupling parts (e.g., one of the links) for attachment to the restraining point 72 thereby controlling the effective length of the strap 76.

Figure 6B:
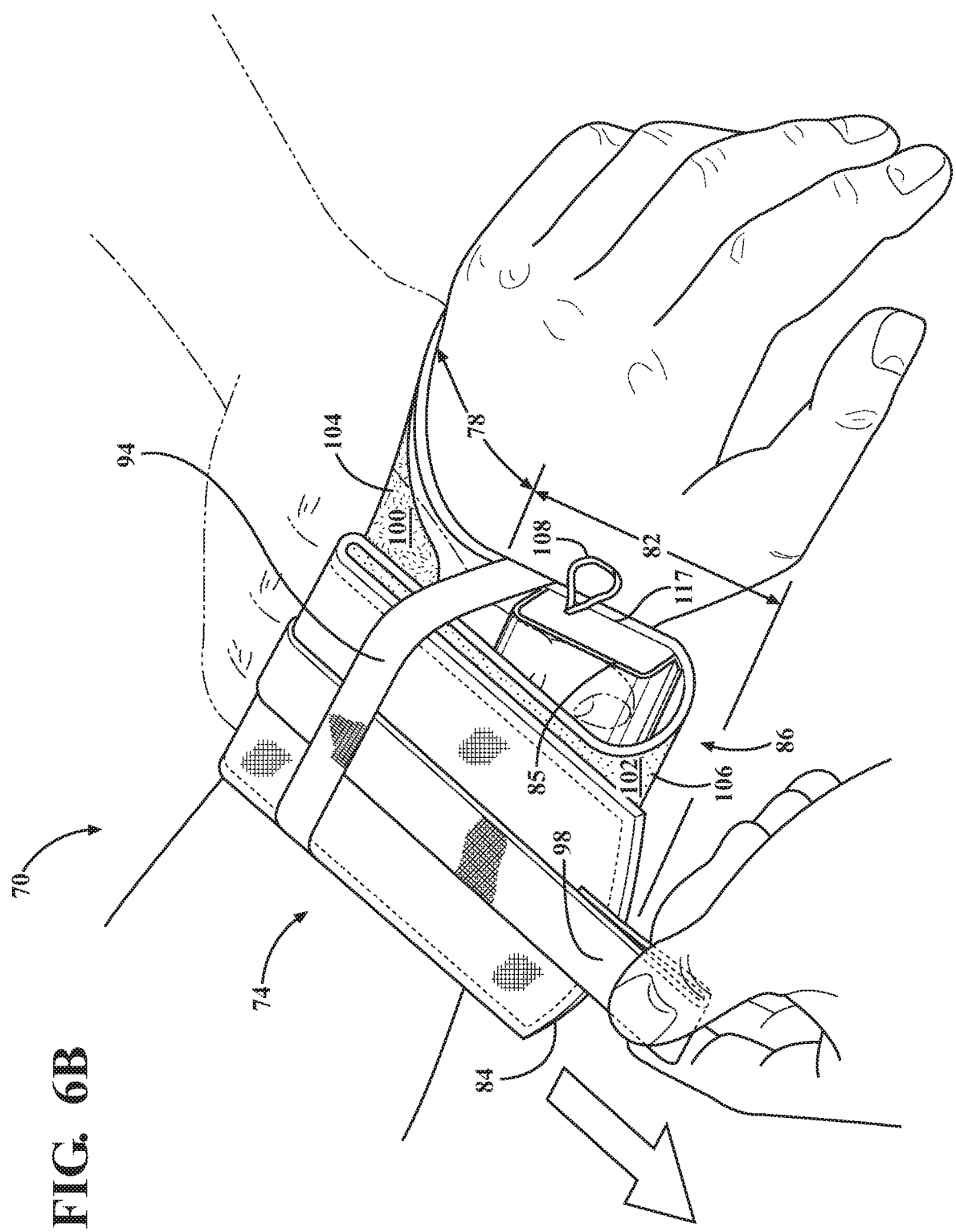
FIG. 6B is a perspective view of another alternative restraint apparatus illustrating a retracting mechanism.

In other embodiments, instead of the tether between the cuff 74 and the restraining point 72 comprising the strap 76, the tether may comprise a cord or rope fixed at one end to the cuff 74 (see FIG. 6B). The tether may be retractable into the storage location 117 via a retracting mechanism 85 similar to that used for a retractable dog leash or a retractable phone cord. See, for example, the retracting mechanism disclosed in U.S. Pat. No. 5,094,396 to Burke, hereby incorporated by reference, which could be fixed to the cuff 74 (e.g., by fasteners, ultrasonic welding, or the like). The tether may also comprise an elastic bungee cord fixed at one end to the cuff 74. Other forms of the tether are also possible. In these embodiments, the tether also comprises the coupler 108 described herein for coupling the cuff 74 to the restraining point 72.

As shown in FIGS. 4 and 5, the strap 76 may be stored in a gathered configuration 114 on the cuff 74 prior to use. In this case, the strap 76 is neatly stored on the cuff 74 until the strap 76 is ready to be deployed for coupling to the restraining point 72. Once ready for deployment, the strap 76 may be extended to an extended configuration 116 (see FIG. 8). The strap 76 may be accordion-style folded or folded in other ways when the strap 76 is in the gathered configuration 114. In other embodiments, the strap 76 could be housed, stored, or otherwise attached to the cuff 74 in other locations or in other ways.

It is contemplated that the cuff 74 comprises at least one storage location 117 configured to store the strap 76 when the strap 76 is in the gathered configuration 114. In the embodiment shown, the storage location 117 is provided by an additional layer 119 of material attached to the first layer 75 on at least two edges to form a pocket 118. The strap 76 may be temporarily fastened inside the pocket 118 when the strap 76 is in the gathered configuration 114. The pocket 118 is sized to hold and store the strap 76 in the gathered configuration 114.

In other embodiments, the storage location 117 may simply be a location on any surface of the cuff 74 to which the strap 76 is temporarily and neatly secured. For example, fasteners, such as hook and look fasteners (e.g., Velcro®), tape, etc. could be used to store the strap 76 on the cuff 74. In one example, the strap 76 may comprise a first hook and loop fastener affixed thereto (e.g., hooks) and the storage location may comprise a mating, second hook and loop fastener (e.g., loops) to secure the strap 76. One or more tabs (not shown) may be attached at predefined locations on the strap 76 and may protrude out of the pocket 118 (or other storage location) to enable the user to easily locate and pull the strap 76 away from the storage location 117. In some embodiments, the strap 76 may be elastic and/or pre-coiled (like a telephone cord) and be packed in the storage location 117 for retrieval at the appropriate time.

Figure 7A:
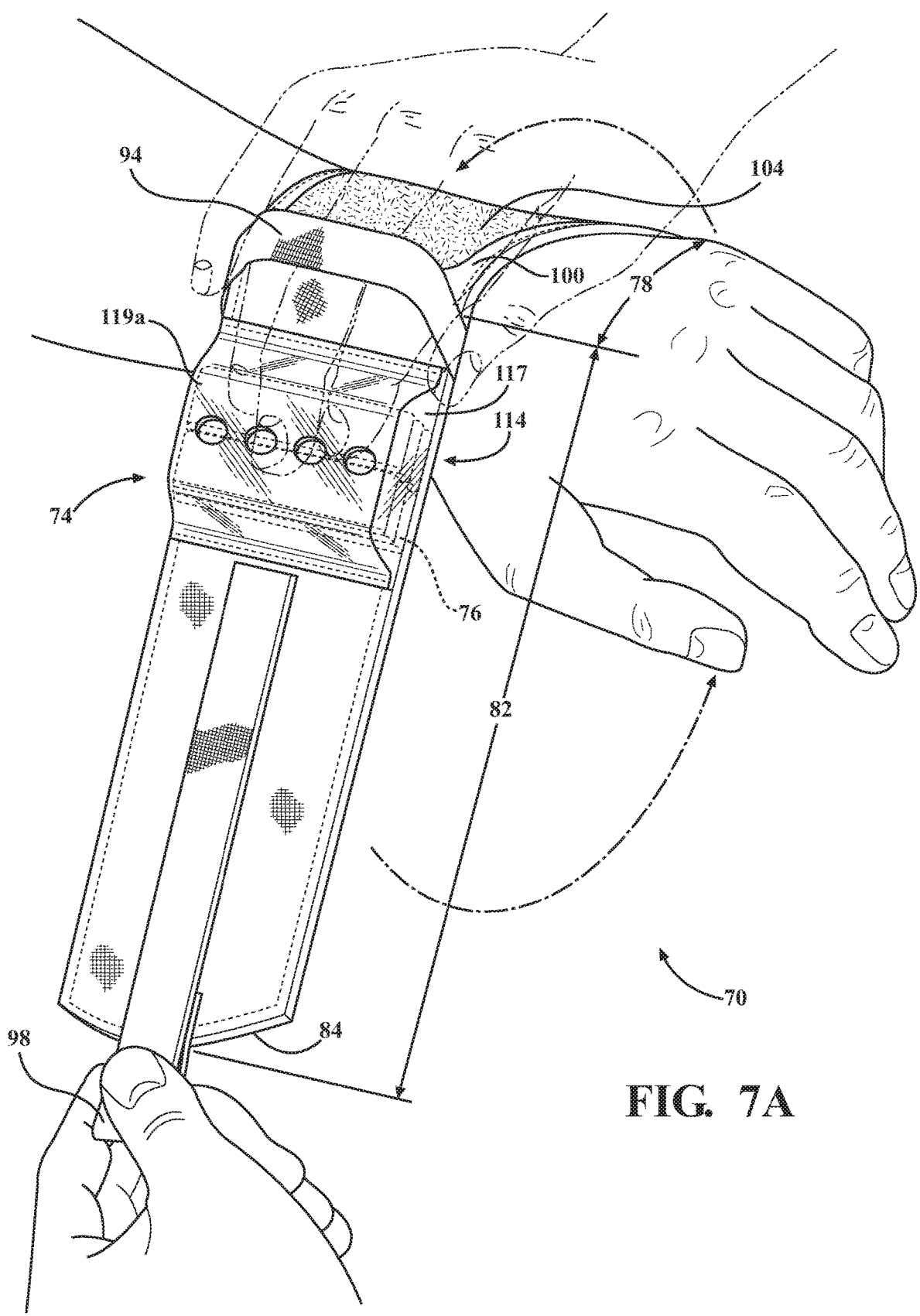
FIG. 7A is a perspective view of the restraint apparatus illustrating an alternative storage location for a tether.
Figure 7B:
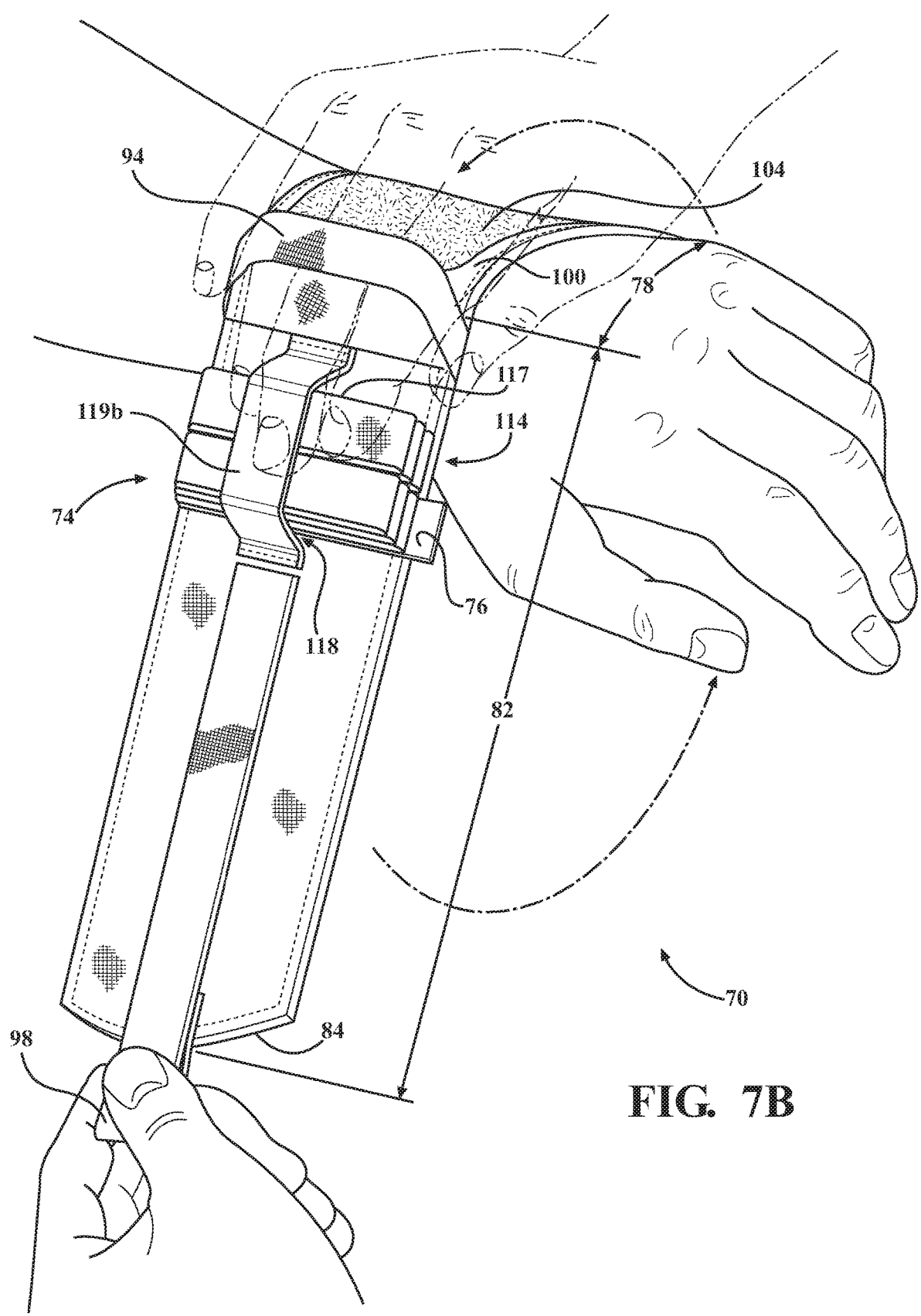
FIG. 7B is a perspective view of the restraint apparatus illustrating another alternative storage location for the tether.

Referring to FIGS. 7, 7A, and 7B, various embodiments of the additional layer of material 119, 119a, 119b are shown. The additional layer of material 119, 119a, 119b may comprise any suitable material, such as fabric, plastic, rubber, paper, combinations thereof, and the like. The additional layer of material 119, 119a, 119b may be elastic, inelastic, or semi-elastic. The additional layer of material 119, 119a, 119b may resiliently hold the strap 76 in place at the storage location 117. The additional layer of material 119, 119b may only partially surround the strap 76 (see FIG. 7B) or the additional layer of material 119a may fully encompass the strap 76 (see FIG. 7A). The additional layer of material 119a may comprise a tear-away membrane, such as that shown in FIG. 7A, which has perforations to allow the user to tear-away the membrane and access the strap 76 in its storage location 117. The membrane may comprise one or more tabs (not shown) protruding outwardly to facilitate tearing away the membrane. In further embodiments, part of the strap 76 may protrude through the membrane at the top and/or sides thereof to facilitate tearing the membrane when pulling the strap 76 out from the storage location 117. The additional layer of material 119a may also be of such minimal thickness or strength that it can be ripped without needing perforations, yet be suitable to hold the strap 76 in place on the cuff 74 until needed.

Referring again to FIG. 1, the restraining point 72 may be coupled, fixed, or otherwise attached to the patient support apparatus 30. The restraining point 72 may comprise one or more of a hook, a carabineer, a climbing stopper, a cam cleat having a catch, a D-ring, a magnetic catch mechanism, or other mechanism configured to engage with the coupler 108 in order to attach the strap 76 to the patient support apparatus 30. The restraining point 72 may also comprise multiple coupling parts, such as a chain of links like that previously described.

The coupler 108 and restraining point 72 are configured in some embodiments so that the coupler 108 is unable to be removed from the restraining point 72 without additional manipulation. For instance, the coupler 108 may be a loop that can be quickly attached to a carabineer at the restraining point 72, but the loop cannot be removed without actuating the carabineer. It may be desirable in some cases for the coupler 108 to be capable of attaching to the restraining point 72 with one-handed operation. Additionally, it may be desirable for the coupler 108 and the restraining point 72 to be configured so that the coupler 108 is unable to be easily disconnected from the restraining point 72 with one-handed operation. In other embodiments, the restraining point 72 can be attached to any secured structure including but not limited to a wall, an emergency vehicle, and the like.

The components of the restraining point 72 and the coupler 108 may comprise any suitable components capable of being coupled together so long as the strap 76 couples the cuff 74 to the restraining point 72. In further embodiments, the strap 76 is permanently affixed at one end to the patient support apparatus 30 with the coupler 108 attached to or otherwise located at the other end of the strap 76. In this case, the strap 76 is initially disconnected from the cuff 74 until the cuff 74 is wrapped around the limb of the person to be restrained. The cuff 74 has a coupling point (not shown) to which the coupler 108 on the strap 76 can then be attached. In this embodiment, the coupling point may simply comprise a loop of material, a D-ring, or the like, to which the coupler 108 on the strap 76 can be attached. Furthermore, in this embodiment, it is contemplated that the strap 76 may be extendable from or retractable into a retracting mechanism (not shown) disposed on the patient support apparatus 30.

As illustrated in FIG. 1, the restraining point 72 may be permanently fixed to the patient support apparatus 30 on the intermediate frame 36, on or below the side rail 44, 46, 48, or may be fixed at any other point as desired. Moreover, the restraining point 72 may be part of the intermediate frame 36 itself. Additionally, multiple types of restraining points 72 may be provided (as shown in FIG. 1) giving the user an option of alternative restraining points 72 for the strap 76 based on convenience or distance. Additionally, the restraining points 72 may be laterally extended away from the intermediate frame 36 so that the user is able to easily couple the strap 76 to the restraining points 72.

In some embodiments, it may be desired that the cuff 74 and/or the strap 76 be free from any exposed hard surfaces which could be used as a weapon by the user or the person, such as any metal, D-rings, hooks, clips, etc.

In operation, referring first to FIG. 5, the cuff 74 starts in the open configuration 86. The strap 76 is disposed in the pocket 118 in the gathered configuration 114. The cuff 74 is engaged by the hand of the user by placing one, two, three, four, or five fingers beneath a folded portion of the second section 82 which is secured in the folded configuration 92 by the engaging element 94, the temporary fasteners 96, or both.

Once the cuff 74 is secured onto the hand of the user, the user grabs the limb of the person to be restrained, as shown in FIG. 6. When the user grabs the limb, the cuff 74 is disposed between the limb of the person and the hand of the user. Additionally, when the user grabs the limb of the person, the first section 78 of the cuff 74 may at least partially surround the limb of the person to further facilitate securing the cuff 74 on the limb. However, in the embodiment shown, the first section 78 does not fully encircle the limb of the person.

Once the limb of the person is grasped by the hand of the user, the opposite hand of the user transitions the cuff 74 from the open configuration 86 to the closed configuration 88 using the tab 98, as shown in FIG. 7. The user pulls the tab 98 disposed on the second section 82 with the opposite hand, or may simply pull the second section 82 itself to transition the cuff 74 from the open configuration 86 to the closed configuration 88. The user then secures the second fastener 106 to the first fastener 104 to secure the cuff 74 completely around the limb of the user while simultaneously releasing the user's hand from the cuff 74. Additional fastening may be provided to ensure that the cuff 74 is not easily removed by the person to be restrained. This may comprise placing the engaging element 94 over the second end 84, with, for example, the engaging element 94 having additional fastening features to attach to the second section 82, such as additional hook and loop fasteners, snaps, adhesive or the like. In some embodiments, the cuff 74 may be wrapped multiple times around the wrist of the person being restrained.

The cuff 74 is now disposed on the person's forearm. The user may then pull the strap 76 from the storage location 117 thereby transitioning the strap 76 from the gathered configuration 114 to the extended configuration 116. It is contemplated that either hand of the user may transition the strap 76 from the gathered configuration 114 to the extended configuration 116. However, it is contemplated that the hand of the user which engaged the cuff 74 and grasped the limb of the person may remain on the limb of the person and the opposite hand of the user may transition the strap 76 from the gathered configuration 114 to the extended configuration 116. In the extended configuration 116, the strap 76 is coupled to the restraining point 72 (see FIG. 1) by engaging the restraining point 72 with the coupler 108. Once the strap 76 is coupled to the restraining point 72, the user can then adjust the effective length of the strap 76 to the desired length to fully restrain the limb. Additional restraint apparatuses 70 may be used to restrain each of the limbs of the person. In some cases, it may be necessary to employ four restraint apparatuses 70 to restrain each wrist and ankle to separate restraining points 72 on the patient support apparatus 30. Additionally, more than one restraint apparatus 70 could be used for each limb.

Referring now to FIGS. 9-17, alternative restraint apparatuses 130 are shown. The restraint apparatuses 130 comprise cuffs 131 configured to be wearable on the hand of the user. The cuffs 131 may comprise any of the layers and/or materials previously described above for the cuff 74. In these embodiments, the cuff 131 comprises a glove 132. The glove 132 may be a standard glove including five finger sections 134 or may be a partial glove having one or more finger sections, similar to a mitten. As illustrated in the embodiment shown in FIGS. 9 and 10, the glove 132 may include multiple finger sections 134 along with a mitten-like portion configured to house multiple fingers in a single section. The glove 132 or partial glove may additionally have at least a portion of the finger sections 134 removed such that one or more fingers of the user are exposed when the glove 132 is worn on the hand of the user, as illustrated in the embodiments shown in FIGS. 11 and 12.

Referring to FIGS. 9 and 10, the cuff 131 comprises a first strap 136, a second strap 138, and a third strap 140. The first strap 136 is coupled to a top surface 142 of the glove 132. A first end portion 146 of the first strap 136 may be coupled permanently to the top surface 142 of the glove 132, while a second portion 148 of the first strap 136 is able to be releasably attached to the top surface 142 of the glove 132. The second portion 148 of the first strap 136 is configured to be releasably attached to the top surface 142 of the glove 132 at a first fastening location 150. The first fastening location 150 may be disposed along the entire top surface 142 of the glove 132 or along any portion of the top surface 142 of the glove 132.

The second strap 138 is coupled to a bottom surface 144 of the glove 132. Specifically, a first end portion 152 of the second strap 138 may be coupled permanently to the bottom surface 144 of the glove 132. A second portion 154 of the second strap 138 may be configured to be releasably attached to the bottom surface 144 of the glove 132. Specifically, and as illustrated in FIG. 10, the second portion 154 of the second strap 138 is configured to be releasably attached to the bottom surface 144 of the glove 132 at a second fastening location 156. The second fastening location 156 may be disposed along the entire bottom surface 144 of the glove 132 or along any portion of the bottom surface 144 of the glove 132. Additionally, the second portion 154 of the second strap 138 comprises a connection area 157 configured to engage the second fastening location 156.

The second portions 148, 154 of the first strap 136 and the second strap 138 may be secured to the first fastening location 150 and second fastening location 156, respectively, using hook and loop fasteners or one or more other temporary fasteners including but not limited to plastic tags, snaps, or magnetic lock mechanisms. When both the second portion 148 of the first strap 136 and the second portion 154 of the second strap 138 are secured to the glove 132, the cuff is in an open configuration 158.

Figure 12:
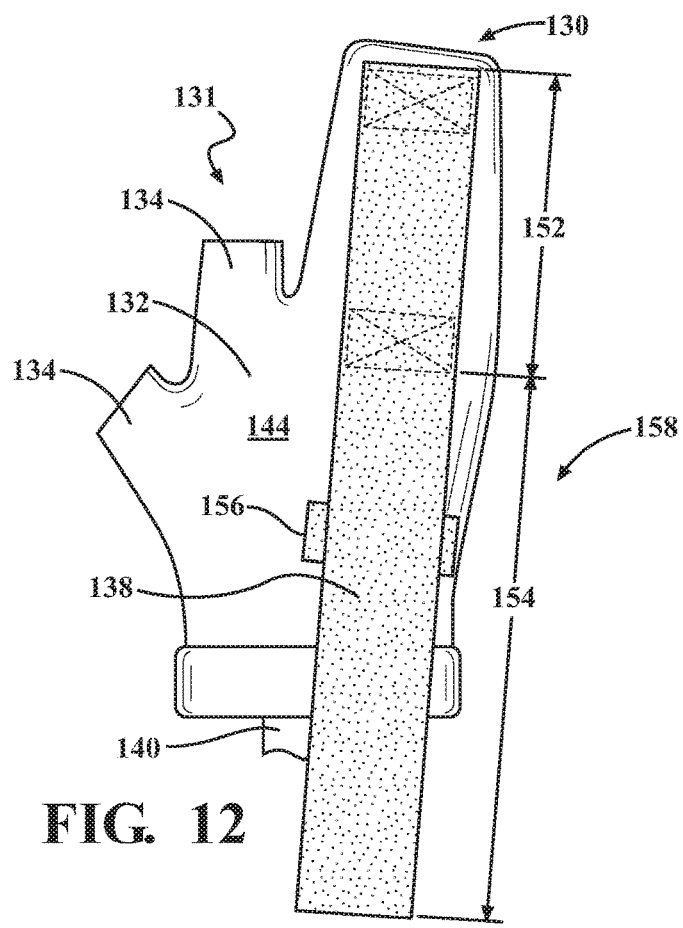
FIG. 12 is a bottom view of the embodiment illustrated in FIG. 11 of the alternative restraint apparatus.

Referring now to the embodiment illustrated in FIGS. 11 and 12, it is contemplated that the second portion 148 of the first strap 136 and/or the second portion 154 of the second strap 138 may extend beyond a wrist portion of the glove 132 in the open configuration 158 in order to provide additional length to the straps so that the first strap 136 and the second strap 138 easily fit around the limb of the person. It is additionally contemplated that the first end 146 of the first strap 136 and/or the first end 152 of the second strap 138 may be fixed to the top surface 142 or bottom surface 144, respectively, of the glove 132 in more than one location in order to provide additional strength to the first strap 136 or the second strap 138.

The third strap 140 may include the features as described above with respect to the strap 76. The third strap 140 is configured to couple the cuff 131 to the restraining point 72. A coupler 162 (see FIG. 14) is located on the third strap 140 to attach the third strap 140 to the restraining point 72. The coupler 162 may be the same as the coupler 108.

The third strap 140 may be attached to any portion of the glove 132, including but not limited to, the top surface 142, the bottom surface 144, or an inside of the glove 132. In the embodiments illustrated in FIGS. 9-14, the third strap 140 is attached to the inside of the glove 132 and extends outward from the glove about the wrist of the user. It is contemplated that the third strap 140 may be disposed in a pocket disposed on the inside of the glove 132, or otherwise disposed inside of the glove 132, such that when the user removes his/her hand from the glove 132 once the glove 132 is in the closed configuration, the hand of the user can easily grab the third strap 140 and couple the third strap 140 to the restraining point 72.

In operation, the restraint apparatus 130 is placed on the hand of the user via the glove 132 with the cuff 131 in the open configuration 158. The user grabs the limb of the person with his/her hand positioned in the glove 132. The user transitions the cuff 131 to the closed configuration 160 by moving the second strap 138 around the limb of the person to engage the third fastening location 161. The user then moves the first strap 136 to engage the connection area 157 and further secure the cuff 131 to the limb of the person by forming an interlocking arrangement around the limb of the person. The user can then remove his/her hand from the glove 132. Before or after removing his/her hand from the glove 132, the user can grasp the third strap 140 disposed inside of the glove 132 and extend the third strap 140 outside of the glove 132. The user then couples the third strap 140 to the restraining point 72 in order to secure the limb of the person to the restraining point 72. Once the third strap 140 is coupled to the restraining point 72, the user can then adjust the length of the third strap 140 to the desired length to fully restrain the limb of the person.

Figure 15:
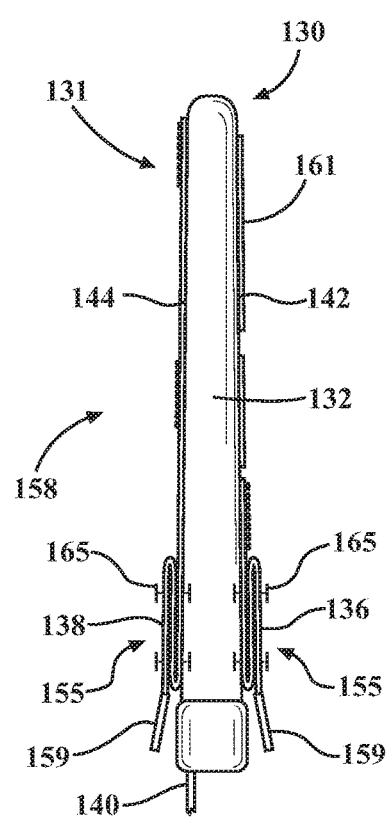
FIG. 15 is side view of a third embodiment of the alternative restraint apparatus.
Figure 13:
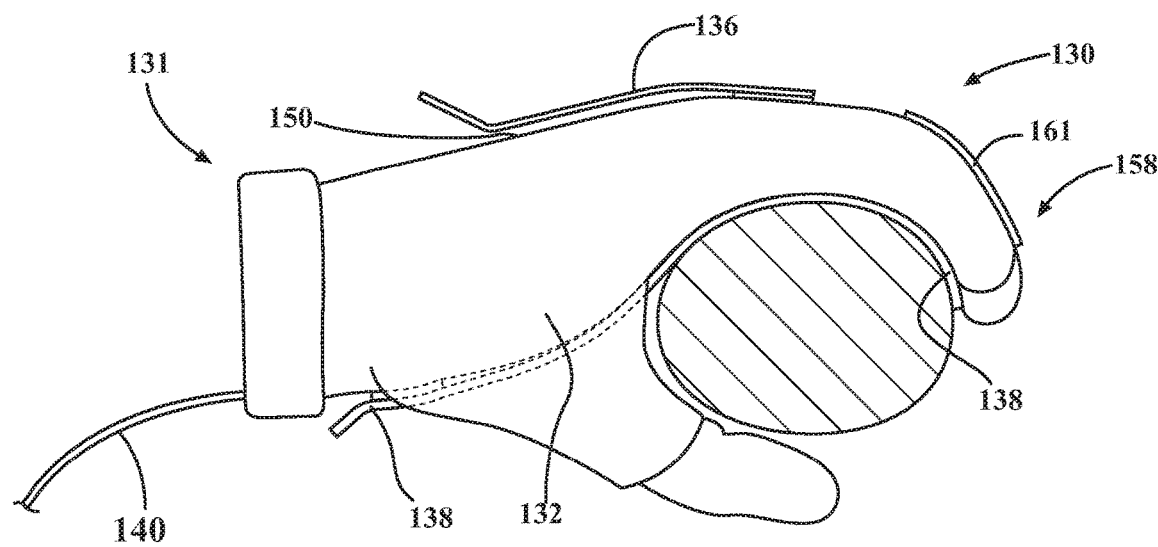
FIG. 13 is a side view illustrating the alternative restraint apparatus in an open configuration about the limb of the person.
Figure 14:
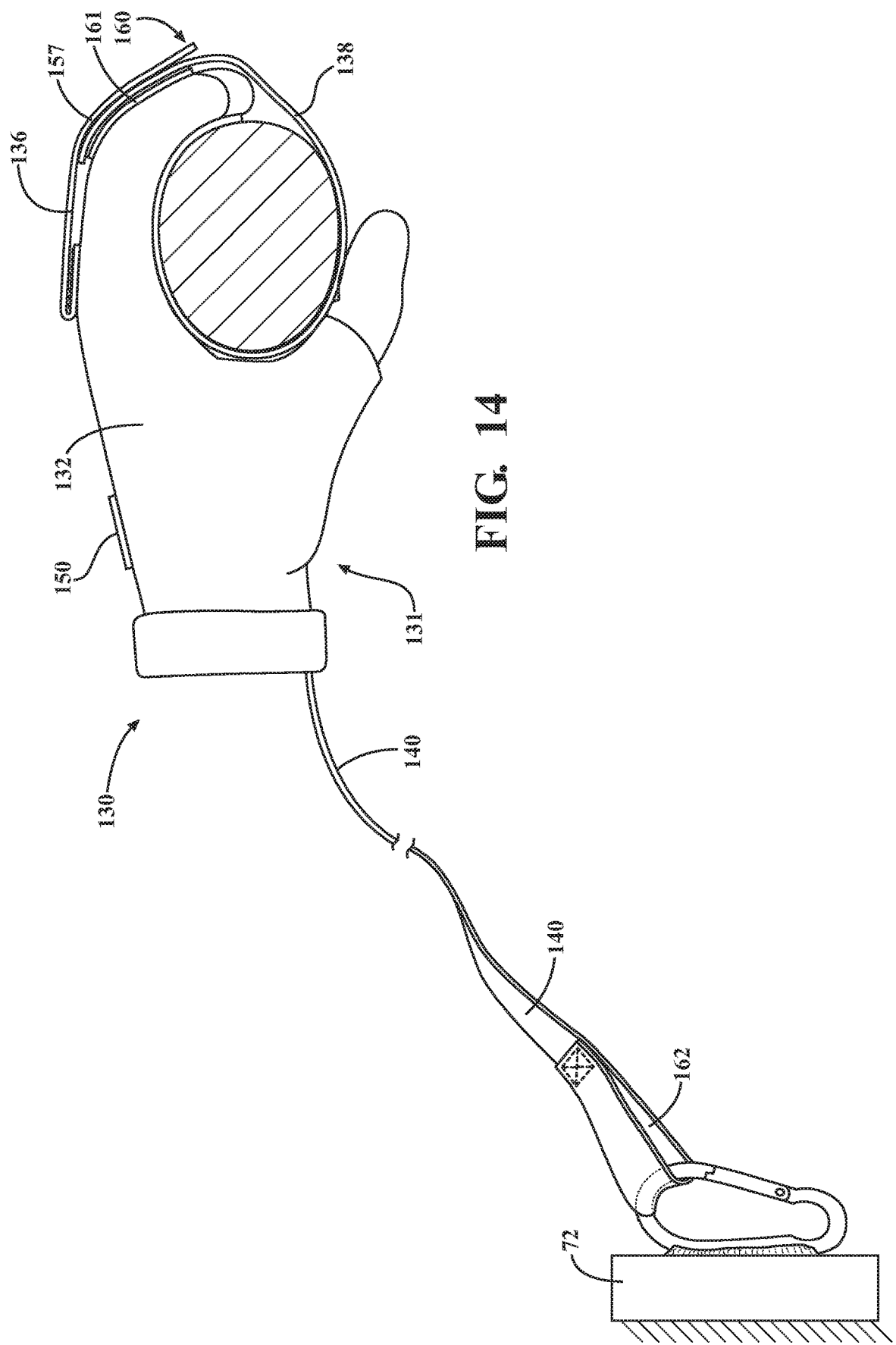
FIG. 14 is a side view illustrating the alternative restraint apparatus in a closed configuration secured about the limb of the person.
Figure 16:
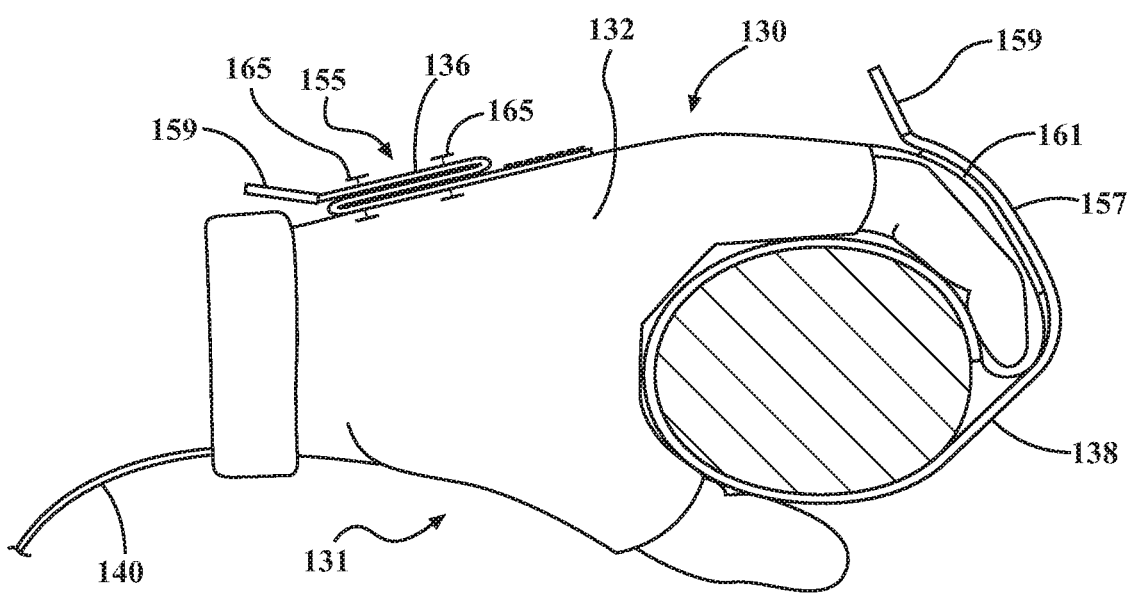
FIG. 16 is a side view illustrating the third embodiment of the alternative restraint apparatus in a closed configuration about the limb of the person.
Figure 17:
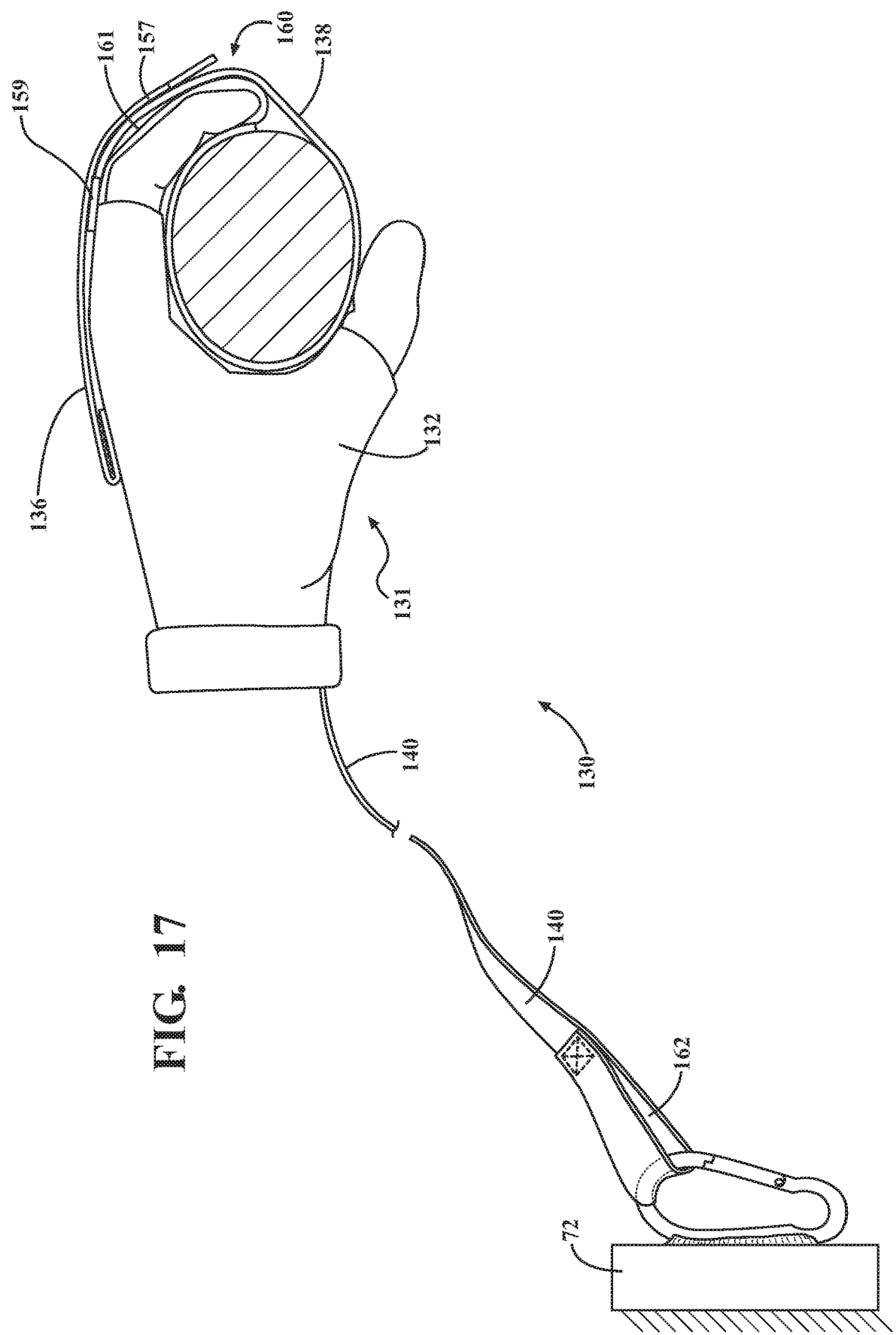
FIG. 17 is a side view illustrating the third embodiment of the alternative restraint apparatus in a closed configuration secured about the limb of the person.

Referring now to the embodiment illustrated in FIGS. 15-17, the alternative restraint apparatus 130 shown includes many of the same features described above with respect to the embodiments shown in FIGS. 9-14. However, in the embodiment illustrated in FIGS. 15-17, in the open configuration 158 the first strap 136 and the second strap 138 are in a folded configuration 155. The first strap 136 and the second strap 138 may be secured in the folded configuration 155 by any number of temporary fasteners 165. The temporary fasteners 165 may be one or more of a hook and loop fastener, plastic tags, snaps, or magnetic lock mechanisms. As illustrated in the embodiment shown in FIGS. 15-17, in the folded configuration 155 each of the first strap 136 and the second strap 138 may include a non-secured portion which forms a tab 159. The tabs 159 may be configured to be engaged by a user to move the first strap 136 and the second strap 138 from the open configuration 158 to the closed configuration 160.

Referring to the embodiment illustrated in FIGS. 15-17, in operation, the restraint apparatus 130 is placed on the hand of the user via the glove 132 with the cuff 131 in the open configuration 158 having the first strap 136 and the second strap 138 in the folded configuration 155. The user grabs the limb of the person with his/her hand positioned in the glove 132. The user transitions the cuff 131 to the closed configuration 160 by moving the second strap 138 to engage the third fastening location 161 around the limb of the person (FIG. 16). The user then moves the first strap 136 to engage the connection area 157 and completely enclose the limb of the person (FIG. 17). Specifically, the opposite hand of the user moves the second strap 138 to engage with the third fastening location 161 and moves the first strap 136 to engage with the connection area 157 of the second strap 138 forming an interlocking arrangement which encloses the limb of the person. The user can then remove his/her hand from the glove 132. Before or after removing his/her hand from the glove 132, the user can grasp the third strap 140 and couple the third strap 140 to the restraining point 72 in order to secure the limb of the person to the restraining point 72. Once the third strap 140 is coupled to the restraining point 72, the user can then adjust the length of the third strap 140 to the desired length to fully restrain the limb of the person.

The cuffs 74, 131 disclosed herein may be single use or may be reusable.

Figure 18:
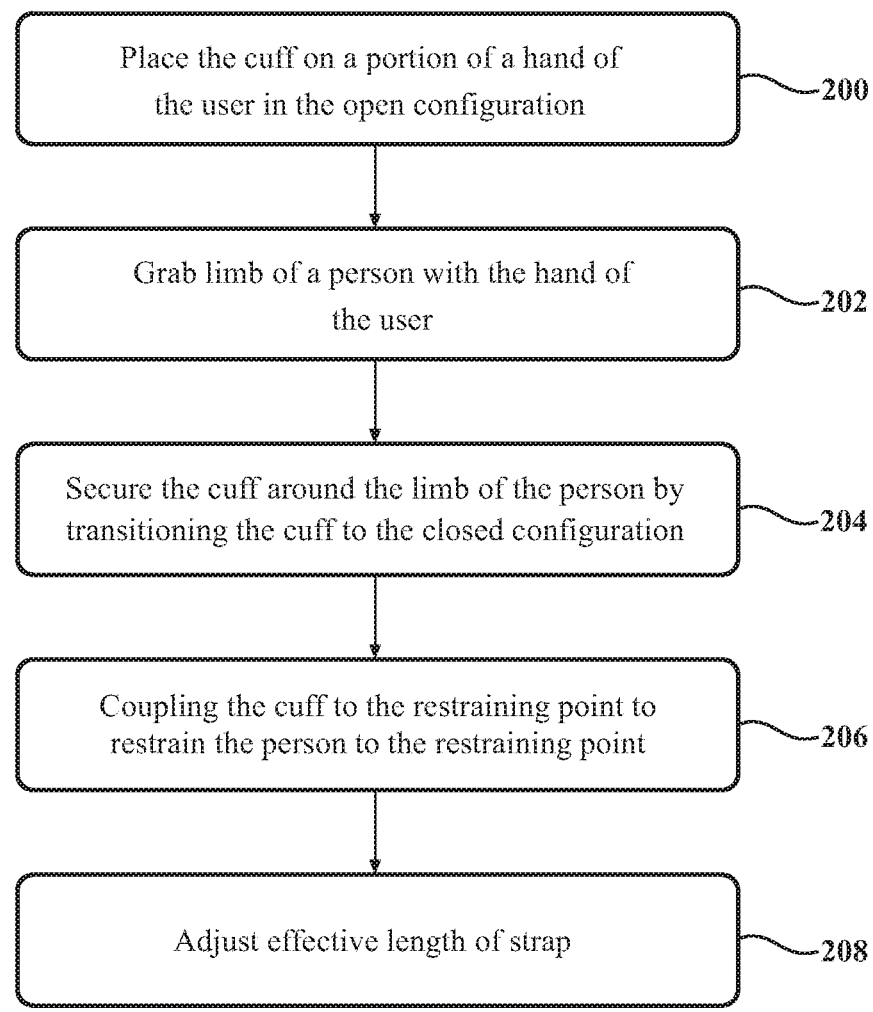
FIG. 18 is a flow chart illustrating steps of one method of restraining a person using the restraint apparatus.

Referring to FIG. 18, a method of using any of the cuffs 74, 131 previously described is outlined. In a first step 200, the cuff 74, 131 is placed on a portion of a hand of the user in the open configuration. In step 202, the user grabs the limb of a person to be restrained with the hand of the user such that the cuff 74, 131 is located between the hand of the user and the limb. In step 204, the cuff 74, 131 is secured around the limb of the person to be restrained by transitioning the cuff 74, 131 to the closed configuration. In step 206, the cuff 74, 131 is coupled to the restraining point 72 with the strap 76 to restrain the person to the restraining point 72. An effective length of the strap 76 can then be adjusted in step 208.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A restraint apparatus operable by a caregiver for restraining a limb of a patient to a restraining point, said restraint apparatus comprising:
    a cuff comprising a first end and a second end, said cuff operable between an open configuration and a closed configuration, wherein said cuff is configured to be secured around the limb of the patient in said closed configuration and said first end and said second end are separated from each other in said open configuration;
    at least one tether attached to said cuff, said at least one tether comprising a strap and a coupler configured to couple said cuff to the restraining point when said cuff is in said closed configuration around the limb of the patient;
    a pocket attached to said cuff and defining a storage location to hold said strap in a gathered configuration for deployment to an extended configuration to couple said cuff to the restraining point; and
    wherein said cuff is wearable on at least a portion of a hand, wrist, or forearm of the caregiver in said open configuration such that the caregiver is able to place said cuff on the limb of the patient in said open configuration while the caregiver is wearing said cuff; and
    wherein said cuff includes at least one engaging element comprising an elastic member and configured to removably retain said cuff on the hand of the caregiver when said cuff is in said open configuration.

2. The restraint apparatus of claim 1, wherein said cuff is configured to at least partially cover the hand of the caregiver in said open configuration.

3. The restraint apparatus of claim 2, wherein said cuff is configured to at least partially encompass a portion of the hand of the caregiver when said cuff is in said open configuration.

4. The restraint apparatus of claim 1, wherein said cuff is configured to be movable from said open configuration to said closed configuration by an opposite hand of the caregiver.

5. The restraint apparatus of claim 4, wherein said cuff comprises at least one tab configured to be pulled by the opposite hand of the caregiver to transition said cuff from said open configuration to said closed configuration.

6. The restraint apparatus of claim 1, wherein said cuff comprises a preformed curved section.

7. The restraint apparatus of claim 1, wherein said cuff comprises a section shaped to conform to the limb of the patient when said cuff is in said open configuration and is positioned adjacent to the limb of the patient.

8. The restraint apparatus of claim 1, wherein said cuff comprises a section shaped to conform to a palm of the hand of the caregiver when said cuff is in said open configuration.

9. The restraint apparatus of claim 1, wherein said cuff comprises a flexible section.

10. The restraint apparatus of claim 1, wherein said at least one engaging element is additionally configured to hold a section of said cuff in said open configuration.

11. The restraint apparatus of claim 1, wherein said cuff comprises a top surface and a bottom surface, wherein a portion of said top surface engages a portion of said bottom surface when said cuff is in said closed configuration.

12. The restraint apparatus of claim 1, wherein said coupler comprises one or more of a loop, a D-ring, a magnetic lock device, and a carabineer.

13. The restraint apparatus of claim 1, wherein said cuff comprises a retracting mechanism configured to retract said at least one tether.

14. The restraint apparatus of claim 1, wherein said at least one tether further comprises a strap adjuster configured to adjust an effective length of said strap.

15. The restraint apparatus of claim 1, comprising a temporary fastener wherein said second end is folded and temporarily secured with said temporary fastener when said cuff is in said open configuration.

16. A restraint system operable by a caregiver for restraining a limb of a patient, said restraint system comprising:
    a cuff comprising a first end and a second end, said cuff operable between an open configuration and a closed configuration, wherein said cuff is configured to be secured around the limb of the patient in said closed configuration and said first end and said second end are separated from each other in said open configuration;
    a patient support apparatus having a restraining point;
    at least one tether attached to said cuff, said at least one tether comprising a strap and a coupler configured to couple said cuff to said restraining point when said cuff is in said closed configuration and configured to be around the limb of the patient;
    a pocket attached to said cuff and defining a storage location to hold said strap in a gathered configuration for deployment to an extended configuration to couple said cuff to the restraining point; and
    wherein said cuff is wearable on at least a portion of a hand, wrist, or forearm of the caregiver in said open configuration such that the caregiver is able to place said cuff on the limb of the patient in said open configuration while the caregiver is wearing said cuff; and
    wherein said cuff includes at least one engaging element comprising an elastic member and configured to removably retain said cuff on the hand of the caregiver when said cuff is in said open configuration.

17. The restraint system of claim 16, wherein said at least one engaging element is additionally configured to hold a section of said cuff in said open configuration.

18. The restraint system of claim 16, wherein said cuff comprises at least a partial glove which is configured to engage the hand of the caregiver when said cuff is in said open configuration.

19. The restraint system of claim 16, wherein said restraining point is permanently attached to said patient support apparatus.

* * * * *